(12) United States Patent
Seiler et al.

(10) Patent No.: US 8,445,024 B2
(45) Date of Patent: May 21, 2013

(54) PREPARATIONS CONTAINING HYPERBRANCHED POLYMERS

(75) Inventors: Matthias Seiler, Griesheim (DE); Axel Kobus, Langen (DE)

(73) Assignee: Evonik Degussa GmbH, Essen (DE)

( * ) Notice: Subject to any disclaimer, the term of this patent is extended or adjusted under 35 U.S.C. 154(b) by 576 days.

(21) Appl. No.: 12/081,711

(22) PCT Filed: Sep. 26, 2006

(86) PCT No.: PCT/EP2006/066722
§ 371 (c)(1),
(2), (4) Date: Apr. 18, 2008

(87) PCT Pub. No.: WO2007/048672
PCT Pub. Date: May 3, 2007

(65) Prior Publication Data
US 2008/0207871 A1    Aug. 28, 2008

(30) Foreign Application Priority Data

Oct. 25, 2005  (DE) .......................... 10 2005 051 334
Aug. 26, 2006  (DE) .......................... 10 2006 040 123

(51) Int. Cl.
*A61K 9/50* (2006.01)

(52) U.S. Cl.
USPC ........... 424/497; 424/486; 424/490; 424/501; 524/81; 524/599; 524/600; 524/601; 524/908

(58) Field of Classification Search
USPC ........... 524/81, 599, 600, 601, 908; 424/486, 424/490, 497, 501
See application file for complete search history.

(56) References Cited

U.S. PATENT DOCUMENTS

| | | | |
|---|---|---|---|
| 1,975,504 A | 10/1934 | Gastell | |
| 4,043,331 A | 8/1977 | Martin | |
| 4,878,908 A | 11/1989 | Martin | |
| 4,923,720 A | 5/1990 | Lee | |
| 5,041,516 A | 8/1991 | Frechet | |
| 5,136,014 A | 8/1992 | Figuly | |
| 5,183,862 A | 2/1993 | Figuly | |
| 5,196,502 A | 3/1993 | Turner | |
| 5,225,522 A | 7/1993 | Turner | |
| 5,227,462 A | 7/1993 | Turner | |
| 5,266,106 A | 11/1993 | Breton | |
| 5,306,561 A | 4/1994 | Frechet | |
| 5,362,843 A | 11/1994 | Vicari | |
| 5,376,117 A | 12/1994 | Pinchuk | |
| 5,418,301 A | 5/1995 | Hult | |
| 5,658,574 A | 8/1997 | Bahary | |
| 5,663,247 A | 9/1997 | Sorensen et al. | |
| 6,110,590 A | 8/2000 | Zarkoob | |
| 6,143,211 A | 11/2000 | Mathiowitz et al. | |
| 6,207,135 B1 | 3/2001 | Rossling et al. | |
| 6,284,233 B1 | 9/2001 | Simon | |
| 6,379,683 B1 | 4/2002 | Simonnet | |
| 6,432,423 B1 | 8/2002 | Maignan et al. | |
| 6,444,758 B2 | 9/2002 | McNamara | |
| 6,468,506 B1 | 10/2002 | Rossling et al. | |
| 6,475,495 B1 | 11/2002 | Maignan et al. | |
| 6,497,895 B2 | 12/2002 | Uhrich | |
| 6,525,170 B1 | 2/2003 | Wang | |
| 6,582,685 B1 | 6/2003 | Adams | |
| 6,713,011 B2 | 3/2004 | Chu | |
| 6,753,454 B1 | 6/2004 | Smith | |
| 6,790,455 B2 | 9/2004 | Chu | |
| 6,916,758 B2 | 7/2005 | Reneker | |
| 6,991,702 B2 | 1/2006 | Kim | |
| 7,070,836 B2 | 7/2006 | Czado | |
| 7,134,857 B2 | 11/2006 | Andrady | |
| 7,150,789 B2 | 12/2006 | Castovillo | |
| 7,229,944 B2 | 6/2007 | Shao-Horn | |
| 7,264,762 B2 | 9/2007 | Ko | |
| 7,297,305 B2 | 11/2007 | Andrady | |
| 7,323,190 B2 | 1/2008 | Chu | |
| 7,326,043 B2 | 2/2008 | Joo | |
| 7,332,050 B2 | 2/2008 | Kim | |
| 2003/0114553 A1 | 6/2003 | Karim | |
| 2004/0013642 A1 | 1/2004 | Tanaka et al. | |
| 2004/0013675 A1 | 1/2004 | Walton | |
| 2004/0016394 A1 | 1/2004 | Castovillo et al. | |

(Continued)

FOREIGN PATENT DOCUMENTS

| | | |
|---|---|---|
| CA | 2119253 | 11/1998 |
| DE | 199 16 384 A1 | 10/2000 |

(Continued)

OTHER PUBLICATIONS

NIST Retinol Data Sheet, 2008 [online], accessed via the Internet [retrieved on Jan. 25, 2011], URL: <http://webbook.nist.gov/cgi/cbook.cgi?ID=68-26-8&Units=SI>.*

Slomkowski, S.; IUPAC Polymer Division Commission on Macromolecular Nomenclature—Sub-Committee on Macromolecular Terminology and Sub-Committee on Polymer Terminology, 2010, p. 1-35.*

Burgath, et al., "Role of cyclization in the synthesis of hyperbranched aliphatic polyesters," *Macromol. Chem. Phys.* 201(7):782-791 (2000).

Hölter, et al., "Degree of branching in hyperbranched polymers," *Acta. Polymer* 48:30-35 (1997).

Magnusson, et al., "The effect of degree of branching on the rheological and thermal properties of hyperbranched aliphatic polyethers," *Polymer* 43:301-306 (2002).

(Continued)

*Primary Examiner* — Robert Jones, Jr.
(74) *Attorney, Agent, or Firm* — Law Office of: Michael A. Sanzo, LLC (57) ABSTRACT

The present invention relates to preparations comprising at least one low molecular weight substance and at least one hyperbranched polymer, wherein the hyperbranched polymer comprises a hydrophilic core having polyester units and hydrophobic end groups, said hyperbranched polymer having a molecular weight greater than or equal to 6000 g/mol and a hydroxyl number in the range from 0 to 200 mg KOH/g, the degree of branching being in the range from 20 to 70%, and said hyperbranched polymer having a melting point of at least 30° C.

20 Claims, 1 Drawing Sheet

U.S. PATENT DOCUMENTS

| | | | |
|---|---|---|---|
| 2004/0097684 A1 | 5/2004 | Bruchmann et al. | |
| 2004/0097685 A1 | 5/2004 | Bruchmann et al. | |
| 2004/0108608 A1* | 6/2004 | Ju et al. | 264/4.1 |
| 2004/0121003 A1* | 6/2004 | Chickering et al. | 424/465 |
| 2004/0170595 A1 | 9/2004 | Zhao | |
| 2004/0197416 A1 | 10/2004 | Simonnet et al. | |
| 2005/0019923 A1 | 1/2005 | Uchegbu | |
| 2006/0030686 A1 | 2/2006 | Lion | |
| 2007/0020224 A1 | 1/2007 | Vetter | |
| 2007/0036720 A1 | 2/2007 | Walton | |
| 2007/0060734 A1 | 3/2007 | Bruchmann et al. | |
| 2007/0106046 A1 | 5/2007 | Bruchmann et al. | |
| 2007/0160561 A1 | 7/2007 | Ouali | |
| 2007/0213501 A1 | 9/2007 | Bruchmann | |
| 2008/0018015 A1 | 1/2008 | McHugh | |
| 2008/0102127 A1 | 5/2008 | Gao et al. | |
| 2008/0200576 A1 | 8/2008 | Seiler et al. | |
| 2008/0207871 A1 | 8/2008 | Seiler et al. | |
| 2008/0274149 A1 | 11/2008 | Seiler et al. | |
| 2009/0011038 A1 | 1/2009 | Seiler et al. | |
| 2010/0136130 A1 | 6/2010 | Seiler | |

FOREIGN PATENT DOCUMENTS

| | | |
|---|---|---|
| EP | 1 025 901 A1 | 8/2000 |
| EP | 1 034 839 A1 | 9/2000 |
| EP | 1 557 441 A2 | 12/2004 |
| FR | 2 787 729 | 6/2000 |
| WO | WO 93/17060 | 9/1993 |
| WO | WO 96/12754 | 5/1996 |
| WO | WO 97/06825 | 2/1997 |
| WO | WO 98/30604 | 7/1998 |
| WO | WO 00/26267 | 5/2000 |
| WO | WO 00/65024 | 11/2000 |
| WO | WO 03/033027 A2 | 4/2003 |
| WO | WO 03/037337 A1 | 5/2003 |
| WO | WO 03/037383 A1 | 5/2003 |
| WO | WO 03/051281 A2 | 6/2003 |
| WO | WO 2004/028269 A1 | 4/2004 |
| WO | WO 2004/072153 A1 | 8/2004 |
| WO | WO 2005/034909 A2 | 4/2005 |
| WO | WO 2005/055949 A2 | 6/2005 |
| WO | WO 2006/031358 A2 | 3/2006 |
| WO | WO 2006/031388 A2 | 3/2006 |
| WO | WO 2006/038110 A2 | 4/2006 |
| WO | WO 2006/047714 A2 | 5/2006 |
| WO | WO 2007/048672 A1 | 5/2007 |
| WO | WO 2007/055561 A1 | 5/2007 |
| WO | WO 2007/104654 A1 | 9/2007 |
| WO | WO 2007/128629 A1 | 11/2007 |
| WO | WO 2008/128924 A1 | 10/2008 |
| WO | WO 2009/049941 A1 | 4/2009 |
| WO | WO 2009/049992 A1 | 4/2009 |
| WO | WO 2009/133059 A2 | 11/2009 |

OTHER PUBLICATIONS

Smirnova, et al., "Feasibility study of hydrophilic and hydrophobic silica aerogels as drug delivery systems," *Journal of Non-Crystalline Solids* 350:54-60 (2004).

English language abstract for FR 2 787 729.

International Search Report for PCT/EP2006/066722 filed Sep. 26, 2006.

English language translation of the Written Opinion of the International Searching Authority for PCT/EP2006/066722 filed Sep. 26, 2006.

English language translation of the International Preliminary Report on Patentability for PCT/EP2006/066722 filed Sep. 26, 2006.

Chow, T.S., "Molecular Interpretation of the Glass Transition Temperature of Polymer-Diluent Systems," *Macromolecules* 13:362-364 (1980).

Greiner, et al., "Electrospinning: A Fascinating Method for the Preparation of Ultrathin Fibers," *Angew. Chem. Int. Ed.* 46:5670-5703 (2007).

Hawker, et al., "Monodispersed Dendritic Polyesters with Removable Chain Ends: a Versatile Approach to Globular Macromolecules with Chemically Reversible Polarities," *J. Chem. Soc. Perkin Trans.* 1:2459-2469 (1992).

Kim, et al., "The Effect of Molecular Weight and the Linear Velocity of Drum Surface on the Properties of Electrospun Poly(ethylene terephthalate) Nonwovens," *Fibers and Polymers* 5(2):122-127 (2004).

Lin, et al., "Reducing Electrospun Nanofiber Diameter and Variability Using Cationic Amphiphiles," *Polymers* 48:6384-6394 (2007).

McKee, et al., "Correlations of Solution Rheology with Electrospun Fiber Formation of Linear and Branched Polyesters," *Macromolecules* 37:1760-1767 (2004).

Pantoula, et al., "Sorption and Swelling in Glassy Polymer/Carbon Dioxide Systems," *J. of Supercritical Fluids* 37:254-262 (2006).

Seiler, Matthias, "Hyperbranched Polymers: Phase Behavior and New Applications in the Field of Chemical Engineering," *Fluid Phase Equilibria* 241:155-174 (2006).

Turner, et al., "All Aromatic Hyperbranched Polyesters with Phenol and Acetate End Groups: Synthesis and Characterization," *Macromolecules* 26(17):4617-4623 (1993).

Zong, et al., "Structure and Process Relationship of Electrospun Bioabsorbable Nanofiber Membranes," *Polymer* 43:4403-4412 (2002).

Zou, et al.,"Encapsulation and Controlled Release of a Hydrophobic Drug Using a Novel Nanoparticle-Forming Hyperbranched Polyester$^a$," *Macromol. Biosci.* 5:662-668 (2005).

Thesis by S. Suttiruengwong, "Silica Aerogels and Hyperbranched Polymers as Drug Delivery Systems," Erlangen (2005).

English language abstract for European patent reference EP 1 557 441.

English language abstract of German patent document DE 199 16 384 A1.

English language abstract of European patent document EP 1 025 901 A1.

English language abstract of International patent document WO 2007/104654 A1.

English language abstract of International patent document WO 2007/128629 A1.

English language abstract of International patent document WO 2008/128924 A1.

English language abstract of International patent document WO 2009/049941 A1.

English language abstract of International patent document WO 2009/049942 A1.

Gamse, et al., "Erzeugung feinster Partikel durch Einsatz von überkritischen Fluiden," *Chemie Ingenirur Technik* 77(6):669-680 (2005).

English language translation of title and abstract of Gamse, et al. article.

Preliminary Amendment filed Oct. 16, 2012 for copending U.S. Appl. No. 12/596,401.

Office Action mailed on Sep. 18, 2012 for copending U.S. Appl. No. 12/596,401.

Tricaprin Product Information received from <http://www.chemicalland21.com/lifescience/foco/TRICAPRIN.htm> on Sep. 12, 2012.

Tristerin Product Information retrieved from <http://chemicalbook.com/ChemicalProductProperty_EN_CB9110090.htm> downloaded on Sep. 12, 2012.

Tristerin Product Information retrieved from <http://chemicalbook.com/ChemicalProductProperty_EN_CB9110090.htm> downloaded on Dec. 8, 2012.

Tripalmitin Product Information retrieved from <http://www.chemicalbook.com/ChemicalProductProperty_EN_CB9163652.htm> downloaded on Sep. 12, 2012.

Tripalmitin Product Information retrieved from <http://www.chemicalbook.com/ChemicalProductProperty_EN_CB9163652.htm> downloaded on Dec. 8, 2012.

Response to Office Action mailed on Sep. 18, 2012 for copending U.S. Appl. No. 12/596,401, filed Dec. 15, 2012.

* cited by examiner

PREPARATIONS CONTAINING HYPERBRANCHED POLYMERS

CROSS REFERENCE TO RELATED APPLICATIONS

The present application is U.S. national stage of international application PCT/EP2006/066722, which had an international filing date of Sep. 26, 2006, and which was published in German under PCT Article 21(2) on May 3, 2007. The international application claims priority to German application 10 2005 051 334.4, filed on Oct. 25, 2005 and to German application 10 2006 040 123.9, filed on Aug. 26, 2006. These prior applications are hereby incorporated by reference in their entirety.

FIELD OF THE INVENTION

The present invention relates to preparations comprising at least one low molecular weight substance and at least one hyperbranched polymer.

BACKGROUND OF THE INVENTION

Preparations of hyperbranched polymers and low molecular weight substances are known per se. In general, such preparations are used in order to achieve a delayed action of the low molecular weight substance. In addition, such preparations have many kinds of positive properties.

Hyperbranched polymers have been described many times. For example, such polymers are detailed in publication EP-A-0630389. In this publication, especially hyperbranched polyesters which can be used in acrylic resins, saturated polyester and unsaturated polyester resins, epoxy resins, phenol resins, polyurethane resins or dental materials are described. Use of these polymers as a carrier substance in order to release low molecular weight substances in a delayed manner is not described herein.

In addition, hyperbranched polymers are detailed in WO 97/06825. The hyperbranched polymers described herein are in many cases polyamides which can be used in a multitude of applications. What is essential here is that the initiator molecule is an aromatic compound which can be converted to a hyperbranched polymer in a single process step. The hyperbranched polymers thus obtained can be used in a multitude of applications. These include especially construction polymers, fibers, films, polymers for production of bottles, a carrier for medicaments, and membranes and supports for catalysts.

In addition, the preparation of hyperbranched polymers is described in J. Chem. Soc. Perkin Trans. 1992 (pages 2459-2469), wherein the hyperbranched polymer is prepared in a multi-step process.

Macromolecules 1993, 26, pages 4617-4623 details the preparation of an aromatic hyperbranched polyester with phenol and acetate end groups. The synthesis is based on a melt condensation of $A_2B$ monomers, for example, 3,5-bis (trimethylsiloxy)benzoyl chloride and 3,5-diacetoxybenzoic acid.

U.S. Pat. No. 5,041,516 discloses a multi-step process for preparing polyesters from aliphatic and aromatic monomers.

Furthermore, the preparation of polyesters from aromatic and aliphatic monomers is disclosed in U.S. Pat. No. 5,136,014. In addition, the U.S. Pat. No. 5,183,862 describes the preparation of hyperbranched polyesters from aliphatic and aromatic monomers.

In addition, the document U.S. Pat. No. 5,196,502 details the preparation of hyperbranched aromatic polyesters using diacetoxybenzoic acids and monoacetoxydibenzoic acids.

The document U.S. Pat. No. 5,225,522 discloses polybranched polyesters having aliphatic and aromatic groups and processes for their preparation.

In addition, the publication U.S. Pat. No. 5,227,462 describes hyperbranched polyesters which may comprise both aliphatic and aromatic groups.

Compositions for producing inks which comprise hyperbranched polymers are disclosed in U.S. Pat. No. 5,266,106.

The production of surface-functionalized polymer particles is detailed in U.S. Pat. No. 5,306,561.

The publication U.S. Pat. No. 5,362,843 discloses a process for preparing hyperbranched macromolecules.

The publication U.S. Pat. No. 5,418,301 discloses a process for preparing dendritic macromolecules.

In addition, the publication WO 98/30604 describes compositions which may comprise hyperbranched polymers and metal compounds. In this case, polyamidoamines and polyesters in particular are detailed.

In addition, WO 2004/072153 details the use of hyperbranched polymers as a carrier for medicaments, in which the carrier molecule is intended to facilitate retarded release and transport of the medicaments into the cells. In this connection, especially modified dendrimers which have nitrogen-comprising groups are detailed.

In addition, the publication WO 00/065024 describes polymers with cells for encapsulation of hydrophobic molecules. In this case a multitude of hydrophobic radicals is bonded to a polyol core, and the resulting polymer is subsequently converted by means of polyalkylene oxides in order to obtain a water-soluble polymer.

In addition, the publication WO 2005/034909 describes compositions comprising a hyperbranched polymer which is coupled to a biologically active radical.

Furthermore, the publication WO 03/037383 describes preparations which comprise hyperbranched polymers. The hyperbranched polymers detailed are especially polyamidoamines or polypropyleneamines.

In addition, hyperbranched polymers are described in the publication WO 00/06267, the hyperbranched polymers detailed being polyetherimides in particular.

Moreover, preparations which comprise dendritic polymers and active pharmaceutical ingredients are detailed in WO 03/033027, the dendrimer comprising cationic groups.

In addition, the use of hyperbranched polymers for the controlled release of active ingredients is described by Zou et al. Macromol. Biosci. 5 (2005) 662-668. In this case, hyperbranched polymers are provided with ionic groups. The molecular weight of the hyperbranched polymers used is approximately 5500 g/mol, no melting point being specified for the hyperbranched polymer.

Moreover, publications U.S. Pat. No. 6,379,683 and EP 1 034 839 B1 describe nanocapsules which comprise hyperbranched polymers. The hyperbranched polymers have a molecular weight of approx. 4800 g/mol.

In addition, WO 97/14404 describes compositions which comprise dendrimers. However, these dendrimers do not serve to encapsulate substances. Preparations in the sense of the present invention are not described in WO 97/14404.

Compositions which comprise dendritic polyesters are detailed in U.S. Pat. No. 6,284,233. However, the dendritic polyesters do not serve to encapsulate substances.

Preparations in the sense of the present invention are not described in U.S. Pat. No. 6,284,233.

The use of hydroxy-functionalized dendritic polymers in cosmetic compositions is described in WO 01/17485. However, these compositions do not comprise preparations in the sense of the present invention.

The thesis by S. Suttiruengwong "Silica Aerogels and Hyperbranched Polymers as Drug Delivery Systems", Erlangen 2005, describes encapsulated systems which may comprise hyperbranched polymers. However, the polymers described have a molecular weight of at most 4600 g/mol, no melting point being specified for the hyperbranched polymer.

The publication DE 10 2004 026 904 describes hyperbranched polyesters which are useful especially as a constituent of printing inks. However, these hyperbranched polyesters do not serve to encapsulate substances. Preparations in the sense of the present invention are not described in DE 10 2004 026 904.

Furthermore, the publication U.S. Pat. No. 6,525,170 describes hyperbranched polyesters. However, the polyesters of the examples comprise a hydrophobic core. Moreover, the polymers have a molecular weight of approx. 1400 g/mol before various reactions, and the properties of the polymers obtained after the modification are not described in detail. Furthermore, there is a lack of information regarding glass transition temperatures or melting points of the resulting polymers.

Furthermore, the publication US 2002/0002242 discloses hyperbranched polymers which are used for modification of surface properties. In this case the core of these polymers may be hydrophobic, in which case the polymers have ambiphilic properties overall. These polymers do not serve to encapsulate low molecular weight substances. Preparations in the sense of the present invention are not described.

The publication US 2003/0114553 describes dental materials which may comprise star polymers. However, no hyperbranched polymers with a hydrophilic core and hydrophobic end groups are detailed. Preparations for delayed release of low molecular weight compounds are likewise not described.

Furthermore, the document US 2004/016394 describes cosmetic compositions which may comprise hyperbranched polymers. However, the properties of these hyperbranched polymers, especially the molecular weight, the degree of branching, the hydroxyl number or the melting point, are not stated explicitly.

Moreover, hyperbranched polymers are detailed in WO 93/17060. However, these polymers are not described in connection with the controlled release of low molecular weight compounds. Preparations in the sense of the present invention are not detailed.

The publication WO 2006/031388 discloses dendritic polymers which can be used especially in orthopedic applications. However, very many different polymers are detailed, none of the polymers detailed explicitly having all properties of the hyperbranched polymers to be used in the present case. For instance, there is especially a lack of information regarding the melting point of the polymers. Moreover, no hyperbranched polymers having a hydrophilic core, hydrophobic end groups and a molecular weight of at least 6000 g/mol are described.

The publication WO 2006/031358 discloses dendritic polymers which can be used especially in ophthalmic applications. However, very many different polymers are detailed, none of the polymers detailed explicitly having all properties of the hyperbranched polymers to be used in the present case. For instance, there is especially a lack of information regarding the melting point of the polymers. Moreover, no hyperbranched polymers having a hydrophilic core, hydrophobic end groups and a molecular weight of at least 6000 g/mol are described.

Accordingly, it can be stated that a multitude of preparations which comprise hyperbranched polymers and low molecular weight compounds has been described. However, there is the constant desire to provide highly advantageous preparations.

OBJECT OF THE INVENTION

In view of the prior art specified and discussed herein, it was an object of the present invention to provide preparations which have an outstanding property profile.

In particular, the inventive preparations should release the low molecular weight substance in a selected medium very substantially over a long period, and the release should be very substantially constant.

In a further aspect, the release of the low molecular weight substance should be controllable in a very simple and reliable manner.

It was a further object of the present invention to provide preparations which comprise a particularly high content of low molecular weight substance.

In addition, the preparation should exhibit particularly high stability, which allows sensitive low molecular weight substances in particular to be stored over a particularly long period without the properties of the low molecular weight substance being changed significantly. In this case, the preparations should likewise have a high shear stability, such that simple and problem-free processing of the preparations is possible.

These objects and further objects which are not stated explicitly but can be derived in an obvious manner from the connections discussed herein or will arise inevitably therefrom are achieved by virtue of the preparations described herein.

DESCRIPTION OF THE INVENTION

By virtue of a hyperbranched polymer comprising a hydrophilic core having polyester units and hydrophobic end groups, said hyperbranched polymer having a molecular weight greater than or equal to 6000 g/mol and a hydroxyl number in the range from 0 to 200 mg KOH/g, the degree of branching being in the range from 20 to 700, and said hyperbranched polymer having a melting point of at least 30° C., it is possible in a not immediately foreseeable manner to provide preparations comprising at least one low molecular weight substance and at least one hyperbranched polymer which have an improved property profile.

By virtue of the inventive measures, it is possible to achieve one or more of the following advantages:

In a particular aspect, the inventive preparations release the low molecular weight substance in a multitude of media over a particularly long period.

In a further embodiment of the present invention, the low molecular weight substance can be released within a short time after a long storage time.

In both embodiments, the release can be controlled precisely by external parameters, for example temperature, pH, radiation frequency and type of medium surrounding the preparation.

Furthermore, the preparation detailed in the present document enables particularly stable storage of sensitive low molecular weight substances. Accordingly, the substances can be stored in a safe and simple manner, in many cases avoiding risk of fire and/or explosion.

Furthermore, chemically active, especially oxidative, substances can be stored, without these substances becoming active in the medium.

Furthermore, the inventive preparations are surprisingly stable, such that they can be stored over a long period without there being any degradation. In addition, the preparations can be processed in a simple and inexpensive manner owing to the high shear stability.

In addition, according to the low molecular weight substance, the inventive preparations are not harmful to health.

Moreover, the inventive preparations may comprise a particularly high content of low molecular weight substance.

Owing to the highly branched polymer structure and the possibility of adjusting the dissolution properties of the polymer via the number of hydrophobic groups, it is possible, compared to the prior art, to achieve better control over the amount of low molecular weight substance which is released per unit time.

The loading concentration in the inventive preparation of low molecular weight substance per g of carrier polymer may be adjusted specifically to the application owing to the hyperbranched polymer structure and the possibility of adjusting the dissolution properties of the polymer via the number of hydrophobic groups. In this case, it is also possible to achieve loading concentrations which are significantly above the prior art loading concentrations (more than 20% by mass of low molecular weight substance based on the binary system consisting of polymer and low molecular weight substance).

It has been found that, surprisingly, in the case of hyperbranched carrier polymers, the encapsulation processes can be operated with significantly reduced amounts of solvents or compressed gases. The hyperbranched polymer thus can itself function as a solvent/dispersant. The solvent/gas concentrations reduced as a result lead to safer processes compared to the prior art, since hyperbranched polymers cannot form explosive vapors like other prior art solvents.

The inventive preparations comprise a hyperbranched polymer with a hydrophilic core. Hydrophilic means that the core is capable of absorbing a high proportion of water. In a preferred aspect of the present invention, the hydrophilic core is water-soluble. The solubility in water at 90° C. is preferably at least 10% by mass, more preferably at least 20% by mass. This parameter is measured on the basis of the hyperbranched polymer before the hydrophobization, i.e. on the hydrophilic core as such. The measurement can be effected by the so-called flask method, which measures the water solubility of the pure substance.

In this method, the substance (solids must be pulverized) is dissolved in water at a temperature slightly above the test temperature. When saturation has been attained, the solution is cooled and kept at the test temperature. The solution is stirred until equilibrium has been attained. Alternatively, the measurement can be performed directly at the test temperature when appropriate sampling ensures that the saturation equilibrium has been attained. The concentration of the test substance in the aqueous solution, which must not comprise any undissolved substance particles, is then determined by a suitable analysis method.

The hydrophilic core preferably has a hydroxyl number measured before the hydrophobization in the range from 400 to 600 mg KOH/g, more preferably in the range from 450 to 550 mg KOH/g. This property is measured to ASTM E222. In this method, the polymer is reacted with a defined amount of acetic anhydride. Unconverted acetic anhydride is hydrolyzed with water. Subsequently, the mixture is titrated with NaOH. The hydroxyl number corresponds to the difference between a comparative sample and the value measured for the polymer. In this measurement, the number of acid groups of the polymer has to be taken into account.

The hyperbranched polymer of the invention has a core which comprises polyester units. Hyperbranched polymers with polyester units are detailed especially in EP 0 630 389. In general, the hydrophilic core is usually a central unit on which is derived from an initiator molecule having at least two, preferably at least three hydroxyl groups and repeat units on which are derived from monomers having at least one carbonyl group and at least two hydroxyl groups.

Highly branched globular polymers are also referred to in the technical literature as "dendritic polymers". These dendritic polymers synthesized from polyfunctional monomers can be divided into two different categories, the "dendrimers" and the "hyperbranched polymers". Dendrimers have a very regular, radially symmetric generation structure. They are monodisperse globular polymers which—compared to hyperbranched polymers—are prepared in multistep syntheses with a high level of synthesis complexity. The structure is characterized by three different areas:—the polyfunctional core which constitutes the center of symmetry,—various well-defined radially symmetric layers of a repeat unit (generation) and—the terminal groups. In contrast to the dendrimers, the hyperbranched polymers are polydisperse and irregular with regard to their branching and structure. In addition to the dendritic and linear units—in contrast to dendrimers—linear units also occur in hyperbranched polymers.

With regard to the different means of synthesizing dendrimers and hyperbranched polymers, reference is made to Fréchet J. M. J., Tomalia D. A., *Dendrimers and Other Dendritic Polymers*, John Wiley & Sons, Ltd., West Sussex, UK 2001; Jikei M., Kakimoto M., Hyperbranched polymers: a promising new class of materials, *Prog. Polym. Sci.*, 26 (2001) 1233-1285; and Gao C., Yan D., *Hyperbranched Polymers: from synthesis to applications*, Prog. Polym. Sci., 29 (2004) 183-275, which are hereby incorporated as references and are considered to be part of the disclosure of the present invention.

The hyperbranched and highly branched polymers described in these publications are also preferred carrier polymers in the context of the present invention. In this connection, it is preferred that the hyperbranched polymers have at least three repeat units per molecule, preferably at least 10 repeat units per molecule, more preferably at least 100 repeat units per molecule, additionally preferably at least 200 repeat units and further preferably at least 400 repeat units, each of which have at least three, preferably at least four bonding means, and at least 3 of these repeat units, more preferably at least 10 and further preferably at least 20 are each bonded via at least three, preferably via at least four bonding means to at least three, preferably at least four further repeat units.

In various cases, the hyperbranched polymers have not more than 10 000, preferably not more than 5000 and more preferably not more than 2500 repeat units.

In a preferred embodiment, the highly branched polymer has at least three repeat units which each have at least three possible bonding means, in which case at least three of these repeat units have at least two possible bonding means.

In this context, the term "repeat unit" preferably means a constantly repeating structure within the hyperbranched molecule. The term "bonding means" is preferably understood to mean that functional structure within a repeat unit with which bonding to another repeat unit is possible. Based on the examples detailed above of a dendrimer and of a hyperbranched polymer, the repeat unit is a structure with three bonding means (X,Y,Z) in each case:

The individual bonding units can be bonded to one another by condensation polymerization, by free-radical polymerization, by anionic polymerization, by cationic polymerization, by group transfer polymerization, by coordinative polymerization or by ring-opening polymerization.

The terms "initiator molecule" and "repeat unit" are widely known in the technical field. It is thus possible to obtain the hyperbranched polymers to be used in accordance with the invention by polycondensation, in which case, proceeding from a polyhydric alcohol, the carboxylic acid groups of the monomers are converted first. This forms ester groups. Since the monomers comprise at least 2 hydroxyl groups, the macromolecule after each reaction has more hydroxyl groups than before the reaction.

The initiator molecule is preferably an aliphatic polyol with preferably 3, 4, 5, 6, 7 or 8, more preferably 3, 4 or 5 hydroxyl groups.

The initiator molecule is more preferably selected from the group of compounds consisting of ditrimethylolpropane, ditrimethylolethane, dipenta-erythritol, pentaerythritol, alkoxylated pentaerythritol, trimethylolethane, trimethylolpropane, alkoxylated trimethylolpropane, glycerol, neopentyl alcohol, dimethylolpropane and/or 1,3-dioxane-5,5-dimethanol.

In a particular aspect of the present invention, the repeat units are derived from monomers having one carboxyl group and at least two hydroxyl groups. These preferred monomers include especially dimethylpropionic acid, $\alpha,\alpha$-bis(hydroxymethyl)butyric acid, $\alpha,\alpha,\alpha$-tris-(hydroxymethyl)acetic acid, $\alpha,\alpha$-bis(hydroxymethyl)-valeric acid, $\alpha,\alpha$-bis(hydroxy)propionic acid and/or 3,5-dihydroxybenzoic acid.

The hydrophilic core is most preferably obtainable by polymerization of dimethylolpropionic acid, in which case the initiator molecule used is more preferably ditrimethylolpropane, trimethylolpropane, ethoxylated pentaerythritol, pentaerythritol or glycerol.

In a preferred embodiment, the hydrophilic core preferably has a molecular weight of at least 1500 g/mol, preferably at least 2500 g/mol. This parameter is based on the weight-average molecular weight (Mw), which can be measured by means of gel permeation chromatography, the measurement being effected in DMF and polyethylene glycols being used as the reference (cf., inter alia, Burgath et al. in Macromol. Chem. Phys., 201 (2000) 782-791). In this case, a calibration curve which has been obtained using polystyrene standards is used. This parameter therefore constitutes an apparent measurement.

The hydrophilic core may preferably have a glass transition temperature which is in the range from −40 to 60° C., more preferably 0 to 50° C. and most preferably 10 to 40° C. The glass transition temperature can be determined by DSC processes using a heating rate of 3° C./min (DMA Tan δ peak; Netzch DMA 242 3-point bending 1 Hz 3° C./min).

The hydrophobization of the surface is generally obtained as the last reaction step by reacting at least some of the free hydroxyl groups with preferably a long-chain carboxylic acid.

The degree of functionalization of the hyperbranched core molecule with hydrophobic end groups, preferably fatty acid-containing units, is preferably at least 30%, more preferably at least 40%. In a further aspect of the present invention, the degree of functionalization of the hyperbranched core molecule with hydrophobic end groups, preferably fatty acid-containing units, is in the range from 30 to 100%, preferably in the range from 35 to 95%, especially preferably in the range from 40 to 90% and most preferably in the range from 45 to 85%.

The degree of functionalization is based on the proportion of hydroxyl groups which are converted in the hydrophobization. Accordingly, the degree of functionalization or the degree of esterification with fatty acids can be determined via the measurement of the hydroxyl number for the hyperbranched core molecule before the hydrophobization reaction and after the hydrophobization reaction.

In addition to the hydrophilic core, the hyperbranched polymer has hydrophobic end groups. In this connection, the term "hydrophobic end groups" means that at least some of the chain ends of the hyperbranched polymer have hydrophobic groups. In this context, it can be assumed that an at least partly hydrophobized surface is obtained as a result.

The term "hydrophobic" is known per se in the technical field, and the groups which are present at least on some of the ends of the hyperbranched polymers, considered per se, have a low water solubility.

In a particular aspect, the surface is hydrophobized by groups which are derived from carboxylic acids having at least 6, preferably at least carbon atoms. The carboxylic acids preferably have at most 40, particularly at most 32 carbon atoms, more preferably at most 20 carbon atoms and most preferably at most 18 carbon atoms. The groups may be derived from saturated and/or unsaturated fatty acids. The proportion of the carboxylic acids having 12 to 18 carbon atoms is preferably at least 30% by weight, more preferably at least 50% by weight and most preferably at least 60% by weight, based on the weight of the carboxylic acids used for the hydrophobization.

These include especially fatty acids which are present in linseeds, soybeans and/or tall oil. Particularly suitable fatty acids are those which have a low proportion of double bonds, for example hexadecenoic acid, especially palmitoleic acid, and octadecenoic acid, especially oleic acid.

Preferred carboxylic acids in this context have a melting point of at least 35° C., preferably at least 40° C. and more preferably at least 60° C. Accordingly, preference is given to using linear, saturated carboxylic acids. These include especially octanoic acid, decanoic acid, dodecanoic acid, tetradecanoic acid, hexadecanoic acid, heptadecanoic acid, octadecanoic acid, eicosanoic acid, docosanoic acid and tetracosanoic acid. Particular preference is given to saturated fatty acids having 16 to 22 carbon atoms, especially preferably 16 to 18 carbon atoms.

The hyperbranched carrier polymer (after the hydrophobization) has a molecular weight of at least 6000 g/mol, more preferably at least 7500 g/mol. The molecular weight is preferably at most 30 000 g/mol, more preferably at most 25 000 g/mol. This parameter is based on the weight-average molecular weight (Mw), which can be measured by means of gel permeation chromatography, the measurement being effected in DMF and the reference used being polyethylene glycols (cf., inter alia, Burgath et al. in Macromol. Chem. Phys., 201 (2000) 782-791). In this method, a calibration curve which has been obtained using polystyrene standards is used. This parameter is therefore an apparent measurement.

The polydispersity Mw/Mn of preferred hyperbranched polymers is preferably in the range from 1.01 to 6.0, more preferably in the range from 1.10 to 5.0 and most preferably in the range from 1.2 to 3.0, where the number-average molecular weight (Mn) can likewise be obtained by GPC.

The weight ratio of hydrophilic core to the hydrophobic end groups may preferably be in the range from 10:1 to 1:10, more preferably from 1:1 to 1:2.5. This ratio arises from the weight average of the hydrophilic core and the weight average of the hyperbranched polymer.

The viscosity of the hyperbranched polymer is preferably in the range from 50 mPas to 5.00 Pas, more preferably in the range from 70 mPas to 3.00 Pas, where this parameter can be determined by means of rotational viscometry at 110° C. and 30 $s^{-1}$ between two 20 mm plates.

The acid number of the hyperbranched polymer is preferably in the range from 0 to 20 mg KOH/g, more preferably in the range from 1 to 15 mg KOH/g and most preferably in the range from 6 to 10 mg KOH/g. This property can be measured by titration with NaOH (cf. DIN 53402).

In addition, the hyperbranched polymer, after the hydrophobization, has a hydroxyl number in the range from 0 to 200 mg KOH/g, preferably in the range from 1 to 150 mg KOH/g and most preferably in the range from 10 to 140 mg KOH/g. This property is measured to ASTM E222. In this case, the polymer is reacted with a defined amount of acetic anhydride. Unconverted acetic anhydride is hydrolyzed with water. Subsequently, the mixture is titrated with NaOH. The hydroxyl number is calculated from the difference between a comparative sample and the value measured for the polymer. In this case, it is the number of acid groups of the polymer that should be taken into account. This can be done through the acid number, which can be determined by means of the process described above.

The degree of branching of the hyperbranched polymer is in the range from 20 to 70%, preferably 25 to 60%. The degree of branching depends on the components used to prepare the polymer, especially the hydrophilic core, and the reaction conditions. The degree of branching can be determined according to Frey et al., this process being detailed in D. Holter, A. Burgath, H. Frey, Acta Polymer, 1997, 48, 30 and H. Magnusson, E. Malmstrom, A. Hult, M. Joansson, Polymer 2002, 43, 301.

The hyperbranched polymer has a melting point of at least 30° C., more preferably at least 35° C. and most preferably at least 40° C. In a particular aspect of the present invention, the melting point of the hyperbranched polymer may preferably be at most 65° C., especially preferably at most 60° C., more preferably at most 57° C. and most preferably at most 55° C. The melting point can be determined by means of differential scanning calorimetry (DSC), for example with the Mettler DSC 27 HP apparatus and a heating rate of 10° C./min.

The water solubility of the hyperbranched polymer after the hydrophobization is preferably at most 10% by mass, more preferably at most 7% by mass and most preferably at most 5% by mass, measured by the flask method detailed above at 40° C.

In addition, particularly preferred hyperbranched polymers, when mixed with water at a temperature of 60° C. or less, preferably of 50° C. or less and more preferably approx. 48° C., exhibit only liquid-liquid equilibria, but no solid-liquid equilibria or solid-liquid-liquid equilibria, this property being determined by using a mixture of 50% by weight of water and 50% by weight of hyperbranched polymer. The measurement can be effected by means of filter experiments, the mixture being filtered through a filter with a suitable pore size, which is preferably 20 µm or less. In the presence of solid-liquid equilibria or solid-liquid-liquid equilibria, the solid constituents of the equilibria remain in the filter, whereas no residue is observed in the case of liquid-liquid equilibria. This property can be controlled, inter alia, through the degree of functionalization and the carboxylic acids used for hydrophobization. When the hyperbranched polymers have a low degree of functionalization and/or short-chain carboxylic acids, these polymers generally exhibit only liquid-liquid equilibria under the conditions detailed above, but no solid-liquid equilibria.

The hyperbranched polymer preferably consists essentially of hydrogen, oxygen and carbon. The term "essentially" means that further elements are present in the hyperbranched polymer up to at most 10% by weight, more preferably at most 5% by weight.

In a particular aspect of the present invention, the hyperbranched polymer can be degraded enzymatically. This can be achieved, for example, by virtue of the hydrophilic core and/or the hydrophobic shell comprising enzymatically degradable organic ester groups.

Preferred hyperbranched polymers or preparations according to the present invention exhibit enzymatic degradation of three days or less, preferably two days or less and more preferably one day or less. In this case, preparations are degraded with a suitable enzyme, especially a lipase, for example Lipomod 34P (Biocatalyst Lmt., UK) and the time until 50% by weight of the active ingredient has been released is measured. For example, preparations with a loading of from 10 to 20% by weight can be analyzed, in which case preferably 0.22 g of active ingredient-laden polymer particles can be suspended in 15 ml of phosphate buffer (pH 5.01) or in 15 ml of solution of the enzyme Lipomod 34P (Biocatalyst Lmt., UK) in the same buffer (concentration of the Lipomod 34P was 0.5 mg/ml). The samples can be kept in a water bath at 37° C. without mixing. At regular time intervals, for example 5 hours, samples of approx. 2 ml can be taken, and the concentration of the active ingredient can be analyzed with suitable processes, for example HPLC (High-Pressure Liquid Chromatography). In this case, the release of a comparative sample which does not comprise an enzyme is taken into account in order to rule out problems of storage stability under the measurement conditions selected, such that the value specified above arises from the difference between analyzed sample and comparative sample.

The preparation of these hyperbranched polymers is detailed especially in EP 630 389. In general an initiator molecule can be reacted with at least one compound which comprises at least two hydroxyl groups and at least one carboxylic acid group. This affords a hydrophilic core which can be reacted with at least one hydrophobic compound, for example a long-chain carboxylic acid.

In general, the reaction is performed at a temperature in the range from 0° C. to 300° C., preferably from 100° C. to 250° C., and the reaction can be accelerated by known esterification catalysts. These catalysts include, for example, Lewis and Brønsted acids, especially p-toluenesulfonic acid, methanesulfonic acid, trifluoroacetic acid, $BF_3$, $AlCl_3$ and $SnCl_4$; titanium compounds, especially tetrabutyl titanate; zinc powder and/or tin powder.

Preference is given to removing water released in the esterification from the reaction mixture.

In addition to a hyperbranched polymer, the inventive preparations comprise at least one low molecular weight substance. The low molecular weight substance is preferably bound to the hyperbranched polymer by a noncovalent method. This can be done, for example, by ionic or polar interactions or by van der Waals forces.

On the basis of the interaction of hyperbranched polymer and low molecular weight substance, the preparation of the present invention can differ from a conventional mixture of these components.

This interaction can be measured in a known manner. According to the low molecular weight substance, spectroscopic methods are suitable for this purpose in many cases. For example, it is possible in some cases to observe shifts in the infrared spectrum.

In addition, the inventive preparations, compared to a conventional mixture, can exhibit delayed release of the low molecular weight substance into a medium other than the low molecular weight substance of the preparation. The delayed release can be measured according to the method described by Smirnova, I.; Suttiruengwong, S.; Arlt W. "Feasibility study of hydrophilic and hydrophobic silica aerogels as drug delivery systems"; Journal of Non-Crystalline Solids (2004) 54-60.

In general, the time difference in order to obtain an identical concentration of the low molecular weight substance in the medium into which the low molecular weight substance is released is at least 1 minute, preferably at least 5 minutes. In this context, this time difference is based on the measurement of a preparation of the present invention and the measurement of a conventional mixture of these components under identical delayed release conditions. Delayed release means that the conditions are not selected such that the preparation releases the low molecular weight substance as fast as possible. These conditions are familiar to those skilled in the art with knowledge of this application. The values of the conventional mixture can also be determined by separate addition of the components.

In a particular embodiment, the preparation is present in encapsulated form, the term "encapsulation" being known in the technical field. In the encapsulated preparation, for example, the low molecular weight substance can be embedded in a shell which comprises hyperbranched polymer. This can be done, for example, by a matrix encapsulation and/or a core-shell encapsulation.

In a particular aspect of the present invention, the preparation of the present invention may be in the form of particles. In this case, these particles preferably have a size in the range from 1 to 1000 µm, more preferably from 10 to 500 µm.

The form of the particles is not critical per se, but the particles preferably have a spherical form.

In the context of the present invention, the term "spherical" means that the particles preferably have a spherical shape, but it is obvious to the person skilled in the art that, owing to the preparation methods, it is also possible for particles of another shape to be present, or that the form of the particles can deviate from the ideal sphere shape.

Accordingly, the term "spherical" means that the ratio of the longest dimension of the particles to the shortest dimension is not more than 4, preferably not more than 2, these dimensions each being measured through the center of the particles. Preferably at least 70%, more preferably at least 90%, based on the number of particles, are spherical.

The particle size can be determined in a commonly known manner. For this purpose, it is possible, for example, to use microscope images which can be evaluated visually and/or with the aid of computers.

In addition, preferred microparticles have a particularly narrow particle size distribution. Preferably at least 80% by weight of the particles are thus within a size range of at most 200 µm, preferably at most 100 µm, more preferably at most 50 µm.

In a particular aspect of the present invention, preferably 90% of the particles have a size in the range from 1 to 1000 µm, especially preferably from 3 to 800 µm, more preferably from 7 to 700 µm and most preferably from 10 to 500 µm.

The preparations of the present invention may exhibit an outstanding shear stability which can in many cases be influenced via the selection of the hyperbranched polymer and the process conditions in the preparation production. The preparations preferably exhibit a shear stability of 1 minute or longer, preferably 5 minutes or longer, this stability being determined at a load which corresponds to that of an ULTRA-TURRAX stirrer at 15 000 revolutions per minute, preferably 20 000 revolutions per minute. In general, a dispersion, for example in a pharmaceutical oil (paraffin oil WINOG 100 Pharma from Univar GmbH), is prepared here, and the dispersion may contain, for example, 10% by weight of preparation. Before and after the stability measurement, which can be effected, for example, by means of an ULTRA-TURRAX stirrer at 15 000 revolutions per minute, preferably 20 000 revolutions per minute, the particles are analyzed microscopically to assess the particle form, size and distribution. There is shear stability under the aforementioned conditions if no significant changes can be observed.

The storage stability of the inventive preparations is in many cases likewise surprisingly high, and depends on the type and composition of the medium if the preparations are stored in the form of dispersions or emulsions, and/or the storage temperatures. Under preferred storage conditions, preferred preparations can be stored over a long period, for example 10 days or longer, preferably 30 days or longer and more preferably 90 days or longer. This parameter can be measured by the release of active ingredient into a medium or the degradation of the low molecular weight substance. These data are based on the period up to which at most 10% of the low molecular weight substance has been released into a medium in which the preparation can be stored, or the time up to which at most 10% of the low molecular weight substance has been degraded, for example by oxidation.

The low molecular weight substance preferably has a molar mass in the range from 15 g/mol to 1000 g/mol, more preferably 30 g/mol to 800 g/mol and most preferably from 60 g/mol to 500 g/mol.

The molecular substance of the invention can be selected in a wide field. It includes especially compounds which comprise a peroxide group, amino acids, catalysts, dyes and/or pigments, vitamins, monomers, flavorings and/or aromas, biologically active components, especially a medicament, initiators, persulfates, silicones, surfactants, silicas, silanes, enzymes and coenzymes, solvents, fillers, reactive crosslinkers, detergents, hair dyes, concrete additives and plant extracts.

Surprisingly, the preparations of the present invention enable chemically labile compounds in particular, for example initiators and/or persulfates, to be stored and transported reliably, the storage and transport conditions being significantly less demanding than those for solutions or powders of these substances. In this context, the risk of explosions or formation of flames can be reduced to an unexpectedly significant degree.

The preferred biologically active components include especially peptides, vitamins and vitamin precursors, fats and fatty acids, amino acids and amino acid precursors, for example creatine, sugar and sugar derivatives, nucleotides, nucleic acids and precursors and derivatives thereof, for example DNA oligomers and RNA oligomers.

The vitamins include especially vitamin A, vitamins of the B complex, for example vitamin B1, vitamin B2, vitamin B3

(folic acid) and vitamin B12, vitamin C (ascorbic acid), vitamins of the D complex, especially 7-dehydrocholesterol, lumisterol, calciferol, ergocalciferol, cholecalciferol, 22,23-dihydroergocalciferol and sitocalciferol, and vitamin E (tocopherol) and vitamin K (phylloquinone, menaquinone).

The preferred amino acids include especially DL-methionine, L-lysine, L-threonine, L-tryptophan and L-leucine.

In addition, the preparations of the invention may comprise, as the low molecular weight substance, especially flavorings, aromas, natural extracts, flavor-enhancing compounds, aromas identical to nature and enzyme-modified food additives.

The aromas include especially ketones, aldehydes, sulfur compounds, carboxylic esters, alcohols and/or natural extracts.

The ketones to be used with preference include, for example, acetone, acetophenone, 2,6-dimethyl-4-heptanone, 3-decen-2-one, methyl amyl ketone, methyl ethyl ketone, methyl heptyl ketone, methyl nonyl ketone, 4-methyl-2-pentanone, methyl propyl ketone, 1-methyl-4-isopropenyl-6-cyclohexen-2-one (D,L-carvone) and/or propiophenone.

The aldehydes to be used with preference include especially acetaldehyde, butyraldehyde, cinnamaldehyde, decanal, dodecanal, heptanal, hexanal, iso-butyraldehyde, E-2-decenal, E-2-dodecanal, E-2-hexanal, E-2-nonenal, E-2-octenal, 2,4-decadienal, 2,4-dodeca-dienal, 2,4-heptadienal, 2,4-nonadienal and/or 2,4-octadienal.

The sulfur compounds to be used with preference include sulfides, for example dimethyl disulfide, dimethyl trisulfide, diphenyl disulfide, dipropyl disulfide, dipropyl trisulfide, ethyl methyl sulfide, isopropyl disulfide, methyl propyl disulfide, methyl propyl trisulfide, methyl 2-thiofuroate, 4-methylthio-2-butanone, 3-methylthio-1-hexyl acetate, 4-(methyl-thio)-4-methyl-2-pentanone;

thiocarboxylic acids and thiocarboxylic acid derivatives, especially thioesters, for example ethyl 3-(methylthio)butyrate, ethyl thioacetate, methyl 3-(methylthio)propionate, methyl thiobenzoate, methyl thiobutyrate, methyl thiohexanoate, methyl thio-isovalerate, n-propyl thioacetate;

mercaptans, especially hexyl mercaptan, isoamyl mercaptan, isobutyl mercaptan and/or thioketones, for example thiomenthone.

The carboxylic esters to be used with preference include amyl acetate, isoamyl acetate, ethyl acetate, ethyl p-anistate, ethyl formate, ethyl hexanoate, ethyl octanoate, butyric esters, n-hexyl acetate, n-hexyl crotonate, hexyl isovalerate, isoamyl butyrate, isoamyl hexanoate, isobutyl butyrate, isobutyl propionate, methyl benzoate, 2-methylbutyl acetate, methyl cinnamate, methyl decanoate, methyl isovalerate, methyl octanoate, methyl propionate, neryl acetate, neryl isobutyrate, n-octyl acetate, phenethyl acetate, phenethyl isobutyrate, phenethyl isovalerate, phenethyl propionate, phenylpropyl acetate, phenylpropyl hexanoate, n-propyl acetate, n-propyl formate and/or n-propyl isobutyrate.

The alcohols to be used with preference include especially anisyl alcohol, benzyl alcohol, 1-butanol, 1-hexanol, isoamyl alcohol, isobutyl alcohol, nerol, ethanol, phenethyl alcohol, propanol, 2-heptanol, 2-octanol, 3-octanol, 2-nonanol and/or 3-hexanol.

The natural extracts include especially banana extracts, strawberry extracts, cocoa extracts, vanilla extracts, coffee extracts, tea extracts, nut extracts, rum extracts, extracts of citrus fruits, kernel extracts, apple extracts and spice extracts. These extracts may in many cases be obtained commercially. These include especially Cocoa Absolute 14620, Cocoa LC 10167, Cocoa P 11197, Cocoa U88; all obtainable from Degussa AG. Natural extracts in this context are extracts which can be obtained from natural sources or have properties which are similar to these extracts.

In a further aspect of the present invention, natural substance extracts may be used as the low molecular weight substance. Natural substance extracts are extracts which are obtained from the natural substances. The preferred natural substance extracts include compositions which are obtained by extraction of pineapples, apples, bananas, beer, pears, strawberries, citrus fruits, raspberries, currants, coffee, coffee oil, cherries, mangoes, orange oil, passion fruit, rum, sour cherries, sloes and/or pure malt whisky.

In addition, the preparations of the invention may comprise natural and synthetic additives, for example food additives, especially 2-acetyl-3,5(6)-dimethylpyrazine, 2-acetylpyrazine, 2-acetylthiazole, 2,3-diethyl-5-methylpyrazine, 2,3-diethylpyrazine, 2,3-dimethylpyrazine, 2,5-dimethylpyrazine, 2,6-dimethylpyrazine, 2-ethyl-3,5-dimethylpyrazine, 2-ethylfuran, 2-ethyl-3-methylpyrazine, 2-ethyl-5(6)-methylpyrazine, 3-ethylpyridine, 2-methoxy-3-isobutylpyrazine, 2-methoxy-3(5),(6)-methylpyrazine, 2-methoxypyrazine, 2-methylpyrazine, 2-pentylfuran, 2,3,5-trimethylpyrazine and/or Compound 1036 (a commonly known cognac oil substitute).

In addition, the preparations of the invention may comprise enzyme-modified dietary ingredients (EMDIs). These additives are obtainable for a multitude of foods, for example as cheese flavorings under the name CPF® Cheese Paste Flavors, NCF® Powdered Cheesed Flavors, BCF® Liquid Blue Cheese Flavors, FDF® Liquid Cheese Flavors. In addition, EMDIs are obtainable as butter flavorings, for example LBO® Butterfat/Cremepaste Flavors; NBF® Powdered Butterfat Flavors; FDF®/DCF® Liquid Butter Flavors.

The preferred compounds having a peroxide group include especially $H_2O_2$, persulfates and/or organic peroxides.

The monomers include especially olefins, for example 1-butene, 1-hexene, norbornene;

vinyl halides, for example vinyl chloride, vinyl fluoride, vinylidene chloride and vinylidene fluoride;

vinyl esters such as vinyl acetate;

styrene, substituted styrenes with an alkyl substituent in the side chain, for example α-methylstyrene and α-ethylstyrene, substituted styrenes with an alkyl substituent on the ring, such as vinyltoluene and p-methylstyrene, halogenated styrenes, for example monochlorostyrenes, dichlorostyrenes, tribromostyrenes and tetrabromostyrenes;

heterocyclic vinyl compounds such as 2-vinylpyridine, 3-vinylpyridine, 2-methyl-5-vinylpyridine, 3-ethyl-4-vinylpyridine, 2,3-dimethyl-5-vinylpyridine, vinyl-pyrimidine, vinylpiperidine, 9-vinylcarbazole, 3-vinyl-carbazole, 4-vinylcarbazole, 1-vinylimidazole, 2-methyl-1-vinylimidazole, N-vinylpyrrolidone, 2-vinyl-pyrrolidone, N-vinylpyrrolidine, 3-vinylpyrrolidine, N-vinylcaprolactam, N-vinylbutyrolactam, vinyloxolane, vinylfuran, vinylthiophene, vinylthiolane, vinyl-thiazoles and hydrogenated vinylthiazoles, vinyl-oxazoles and hydrogenated vinyloxazoles;

vinyl and isoprenyl ethers;

maleic acid and maleic acid derivatives, for example mono- and diesters of maleic acid, maleic anhydride, methylmaleic anhydride, maleimide, methylmaleimide; fumaric acid and fumaric acid derivatives, for example mono- and diesters of fumaric acid;

dienes, for example divinylbenzene;

and acrylates and methacrylates, which are referred to hereinafter as (meth)acrylates.

These include, for example, (meth)acrylates which derive from saturated alcohols, such as methyl(meth)acrylate, ethyl(meth)acrylate, n-propyl(meth)

acrylate, isopropyl(meth)acrylate, n-butyl(meth)acrylate, tert-butyl(meth)acrylate, pentyl(meth)acrylate, hexyl(meth) acrylate, 2-ethyl-hexyl(meth)acrylate, heptyl(meth)acrylate, 2-tert-butylheptyl(meth)acrylate, octyl(meth)-acrylate, 3-isopropylheptyl(meth)acrylate, nonyl(meth)acrylate, decyl (meth)acrylate, undecyl(meth)-acrylate, 5-methylundecyl (meth)acrylate, dodecyl (meth)acrylate, 2-methyldodecyl (meth)acrylate, tridecyl(meth)acrylate, 5-methyltridecyl (meth)-acrylate, tetradecyl(meth)acrylate, pentadecyl (meth)-acrylate, hexadecyl(meth)acrylate, 2-methylhexadecyl (meth)acrylate, heptadecyl(meth)acrylate, 5-isopropyl-heptadecyl (meth)acrylate, 4-tert-butyloctadecyl (meth)acrylate, 5-ethyloctadecyl(meth)acrylate, 3-isopropyloctadecyl(meth)acrylate, octadecyl (meth)acrylate, nonadecyl(meth)acrylate, eicosyl (meth)acrylate, cetyleicosyl(meth)acrylate, stearyl-eicosyl(meth)acrylate, docosyl(meth)acrylate and/or eicosyltetratriacontyl(meth) acrylate;

cycloalkyl(meth)acrylates such as cyclopentyl(meth)acrylate, 3-vinylcyclohexyl(meth)acrylate, cyclohexyl(meth) acrylate, bornyl(meth)acrylate;

(meth)acrylates which derive from unsaturated alcohols, such as 2-propynyl(meth)acrylate, allyl(meth)-acrylate, vinyl (meth)acrylate and/or oleyl(meth)-acrylate;

aryl(meth)acrylates such as benzyl methacrylate or phenyl methacrylate, where the aryl radicals may each be unsubstituted or up to tetrasubstituted;

methacrylates of halogenated alcohols, such as 2,3-dibromopropyl methacrylate, 4-bromophenyl methacrylate, 1,3-dichloro-2-propyl methacrylate, 2-bromoethyl methacrylate, 2-iodoethyl methacrylate, chloromethyl methacrylate.

In addition, preferred low molecular weight substances may originate from the sector of detergents and additives which are used in hair washing compositions and hair colorants, for example acetaminophen, acetylated lanolin alcohol, *Achillea Millefolium, Aesculus Hippocastanum, Agave Rigida, Aloe Barbadensis*, alumina, aluminum chlorohydrate, aluminum formate, aluminum hydroxide, magnesium hydroxide, stearates, especially aluminum stearate and magnesium stearate, aluminum silicate, aluminum tristearate, aminomethylpropanol, ammonia, ammonium bicarbonate, ammonium sulfate, ammoniothioglycolic acid, ammoniothiolactates, amodimethicone, *Anthemis Nobilis, Arachis Hypogaea*.

The preferred catalysts include especially metal-comprising catalysts which are used for hydration or hydrogenation, for example for hardening fatty acids, nitriles and polyol hydrogenation, hydrogenation of resins, aromatics and white oils; selective hydrogenation of acetylenes and dienes and selective hydrogenation of AMS to cumene.

In addition, these include catalysts which are used for oxidation, for example for selective oxidation to prepare ethylene oxide and vinyl acetate monomers; cleaning of offgases from processes, for example for removing CO and VOCs; cleaning of offgases which comprise halogenated hydrocarbons; and the catalysts for cleaning industrial gases.

These catalysts generally comprise metals, for example nickel, cobalt, copper, molybdenum, chromium, iron, and platinum group metals, for example rhodium, palladium, platinum. Such catalysts are known per se and can in many cases be obtained commercially. They especially include products under the trade name catASium® and cataXium® from Degussa.

Examples of these catalysts include (−)-2,3-bis[(2R,5R)-2,5-dimethylphospholanyl]maleic anhydride(1,5-cyclooctadiene)rhodium(I)tetrafluoro-borate (catASium® M(R)Rh);

(−)-2,3-bis[(2R,5R)-2,5-dimethylphospholanyl]-N-methyl-maleimide(1,5-cyclooctadiene)rhodium(I)tetrafluoro-borate (catASium® MN(R)Rh);

(+)-2,3-bis[(2S,5S)-2,5-dimethylphospholanyl]maleic anhydride(1,5-cyclooctadiene)rhodium(I)tetrafluoro-borate (catASium® M(S)Rh);

(+)-2,3-bis[(2S,5S)-2,5-dimethylphospholanyl]-N-methyl-maleimide(1,5-cyclooctadiene)rhodium(I)tetrafluoro-borate (catASium® MN(S)Rh);

(+)-(3R,4R)-bis(diphenylphosphino)-1-benzylpyrrolidine (catASium® D(R));

(+)-(3R,4R)-bis(diphenylphosphino)-1-benzylpyrrolidine (1,5-cyclooctadiene)rhodium(I)tetrafluoroborate (catASium® D(R)Rh);

butyldi-1-adamantylphosphine (cataCXium® A);

benzyldi-1-adamantylphosphine (cataCXium® ABn);

trans-di(mu-acetato)bis[o-(di-o-tolylphosphino)benzyl]-dipalladium (II) (cataCXium® C);

N-phenyl-2-(dicyclohexylphosphino)pyrrole (cataCXium® PCy);

N-phenyl-2-(di-t-butylphosphino)pyrrole (cataCXium® PtB);

1-(methoxyphenyl)(dicyclohexylphosphino)pyrrole (cataCXium® POMeCy);

1-(2,4,6-trimethylphenyl)-2-(dicyclohexylphosphino)-imidazole (cataCXium® PICy).

In relation to the catalysts, the preparations of the invention enable a particularly long and stable shelf life thereof, and particularly simple handling. In addition, the catalysts may be released into the reaction mixture over a particularly long period.

The low molecular weight substances detailed above may be used individually or as a mixture of two, three or more. In this case, the mixtures may comprise low molecular weight substances of the same class or of different classes. For example, a combination may comprise, as a low molecular weight substance, a mixture which comprises a vitamin and a flavoring.

To produce the inventive preparations, the low molecular weight compounds and the hyperbranched polymers may be combined with one another. For this purpose, various methods are suitable, especially coacervation, RESS, GAS and/or PGSS processes, and processes using coaxial nozzles, spray-drying, fluidized bed coating and microencapsulation.

In preferred processes, a compressed gas is used or at least two liquid phases occur, in which case both said phases comprise the low molecular weight substance and at least one liquid phase comprises a hyperbranched polymer.

In the RESS process (Rapid Expansion of Supercritical Solution) a mixture comprising a supercritical fluid and a substance dissolved therein is decompressed abruptly. A more detailed explanation of this process with further evidence is given in Gamse et al., Chemie Ingenieur Technik 77 (2005), No. 6, pages 669 to 679.

In GAS processes, a gaseous or supercritical precipitant is added to a dilute solution of a low molecular weight substance in the presence of hyperbranched polymers. This process can preferably also be operated continuously. These processes have been detailed especially by Gamse et al., Chemie Ingenieur Technik 77 (2005), No. 6, pages 669 to 679 and Tom, J. W.; Lim, G. B.; Debendetti, P. G.; Prod'homme, R. K. Supercritical Fluid Engineering Science, Washington D.C. 1993: Brennecke, J. F.; Kiran, E.; American Chemical Society: 1993.

In the PGSS processes, a compressed gas is added to a solution or a melt. The gas-saturated mixture is then expanded with a nozzle to form solid particles. The PGSS processes have been described, inter alia, by Gamse et al., Chemie Ingenieur Technik 77 (2005), No. 6, pages 669 to 679; Pérez de Diego, Y. Production of Controlled Drug Delivery Microparticles using Supercritical CO2 2004; and Shariati, A.; Peters, C. J. Recent developments in particle design using supercritical fluids. Current Opinion in Solid State & Materials Science 2003, 7 (4-5), 371-383.

In addition, the preparation of the invention can preferably be obtained by PCA processes (Precipitation with Compressed Fluid Antisolvent), wherein a solvent/solid solution is sprayed into a high-pressure chamber, and the phase contact takes place in the spray chamber between the fine droplets and the supercritical fluid, which forms the fine particles (cf. Gamse et al., Chemie Ingenieur Technik 77 (2005), No. 6, pages 669 to 679).

Furthermore, the preparations of the present invention can preferably be produced by means of SEDS processes (Solution Enhanced Dispersion by Supercritical Fluids). In the SEDS process, a liquid stream which comprises the low molecular weight substance and the hyperbranched polymer is likewise obtained. This liquid stream is contacted with the supercritical fluid as early as in the nozzle. By virtue of this process variant, particularly small particles can be obtained (cf. Gamse et al., Chemie Ingenieur Technik 77 (2005), No. 6, pages 669 to 679).

In addition, the preparations of the invention can be obtained or processed further by CPF processes. In the CPF process (Concentrates Powder Form) there is no change in the particle size. The aim of this process is to achieve a high concentration of a liquid in a solid. In this case, the liquids can be contacted with a suitable gas, for example $CO_2$, either in a static mixer before the spraying or dissolved in the case of highly viscous substances, which can achieve a drastic reduction in the viscosity. The ultrafine liquid droplets by means of a nozzle hit the solid metered in in parallel and adhere thereon, such that agglomerates which have high liquid contents can form. In addition, the solid can be impregnated with this liquid (cf. Gamse et al., Chemie Ingenieur Technik 77 (2005), No. 6, pages 669 to 679).

In the above-described processes which work with high pressure, especially the RESS, GAS and/or PGSS processes, the encapsulation can advantageously be effected at temperatures within a range from −20° C. to 250° C., preferably from 0° C. to 180° C. and more preferably from 10° C. to 150° C. The pressure in these processes may be varied over a wide range, and these high-pressure processes can preferably be carried out within a range of from 0.5 bar to 400 bar, more preferably from 1 bar to 200 bar and most preferably from 1 bar to 100 bar.

In the high-pressure processes, the concentration of the low molecular weight component in the hyperbranched carrier polymer may preferably be in the range from 0.5% by mass to 95% by mass, more preferably from 1% by mass to 80% by mass and most preferably from 5% by mass to 50% by mass.

In coacervation, the particles are formed by precipitation from a solution of hyperbranched polymer and low molecular weight substance.

A distinction is generally drawn between simple and complex coacervation, and between aqueous and organic phase separation (R. Arshady, "Microspheres and microcapsules—A survey of manufacturing techniques, Part III: Coacervation", Polymer Engineering and Science 30 (1990) 905 ff). In simple coacervation, one colloidal component, for example gelatin, is used, and, in complex coacervation, two oppositely charged colloidal components, for example gelatin and gum arabic, are used. The principle of coacervation consists in, for example, converting an aqueous gelatin solution, by adding ethanol, to a biphasic system which consists of a gelatin-rich phase (coacervate) and a low-gelatin phase. This is very similar to a polymer fractionation, except that, in this case, microparticles having an average size of 2-5000 micrometers form under the action of shear forces.

The production of microcapsules by coacervation can in many cases be divided into three steps:
(1) generation of (three) immiscible phases,
(2) deposition of the colloid as the capsule shell and
(3) solidifying the capsule shell.

The three immiscible phases include an outer medium, a core material and a capsule shell material. The capsule shell material is dissolved in the outer medium and the core material is dispersed therein. As a result of the action of an external stimulus (temperature, pH, electrolyte), the capsule shell material becomes insoluble in the outer medium and is deposited at the interface to the dispersed core material. After filtration, the capsule shell is finally hardened by the action of heat, crosslinking or solvent removal, or dried by spray-drying or freeze-drying.

Preference is given to performing the coacervation at temperatures in the range from −20° C. to 150° C., more preferably from 0° C. to 100° C. and most preferably from 10° C. to 90° C.

The pressure at which the coacervation takes place is not subject to any particular restriction. In many cases, the coacervation can be performed at a pressure in the range from 10 mbar to 10 bar, preferably from 200 mbar to 5 bar and more preferably from 500 mbar to 3 bar.

The concentration of the low molecular weight component in the hyperbranched carrier polymer may preferably be in the range from 0.5% by mass to 95% by mass, more preferably from 1% by mass to 80% by mass and most preferably from 5% by mass to 50% by mass, without any intention that this should impose a restriction.

This process has been described, inter alia, by R. Arshady, "Microspheres and microcapsules—A survey of manufacturing techniques, Part III: Coacervation", Polymer Engineering and Science 30 (1990) 905 ff.;

Jain, R. A. The manufacturing techniques of various drug loaded biodegradable poly(lactide-co-glycolide) (PLGA) devices. Biomaterials 2000, 21 (23), 2475-2490;

Jung, J.; Perrut, M. Particle design using supercritical fluids: Literature and patent survey. Journal of Supercritical Fluids 2001, 20 (3), 179-219; and Subramaniam, B.; Rajewski, R. A.; Snavely, K. Pharmaceutical processing with supercritical carbon dioxide. Journal of Pharmaceutical Sciences 1997, 86 (8), 885-890.

Spray-drying is a continuously performable process for drying solutions, suspensions or pasty masses. This process is widely known, and systems for performing the process are commercially available. In general, by means of a nozzle (operated by liquid pressure or compressed air or inert gas) or rotating spray disks (4000-50 000 rpm), the material to be dried is introduced into a hot air stream (temperatures up to 220° according to the apparatus) which dries it to a fine powder in fractions of a second. Hot air can flow in the direction of the spray jet or against the spray jet (cocurrent, countercurrent process), according to the design or end use. The spray device is present on the upper part of a spray tower; the dried material obtained is usually separated from the air stream by a cyclone separator and can be withdrawn there.

Microencapsulation is understood to mean the embedding of at least one substance (active ingredient) with the aid of at least one second substance (shell material). The former often cannot be used directly for various reasons (solubility, reactivity, stability, etc.), or particular actions should be achieved by the microencapsulation (e.g. release curves for the controlled release, unique features, etc.).

In practice, there is a series of approaches to microencapsulation, which proceed essentially from two methods, specifically matrix encapsulation and core-shell encapsulation.

For both methods, commercial solutions are obtainable. To this end, formulations and processes individually tailored to the active ingredients are generally used. A commercial supplier of these solutions is BRACE GmbH, Alzenau.

In a preferred aspect of the present invention, the preparations of the invention can be obtained by a process comprising the steps of preparing a polymer melt comprising at least one hyperbranched polymer and at least one low molecular weight substance, introducing the polymer melt into a second liquid phase in which said hyperbranched polymer is sparingly soluble and which has a solidification temperature below the solidification temperature of said hyperbranched polymer, dispersing said polymer melt in said second liquid phase at a temperature which is greater than or equal to the solidification temperature of said hyperbranched polymer, and solidifying said polymer melt dispersed in said second liquid phase.

In the preferred process, a polymer melt is prepared. The term "polymer melt" refers to a free-flowing state of a composition which comprises at least one hyperbranched polymer and at least one low molecular weight substance. The viscosity of the polymer melt is preferably in the range from 50 mPa*s to 5000 Pa*s, more preferably in the range from 100 mPa*s to 1000 Pa*s, this parameter being determinable by means of rotational viscometry. In this context, the free-flowing state is dependent upon factors including temperature. The aforementioned viscosity ranges of the polymer melt are preferably measured at a temperature in the range from 10 to 200° C., more preferably in the range from 50 to 150° C. In a particular aspect of the present invention, the viscosity of the polymer melt may be in the range from 100 mPa*s to 1000 Pa*s, this parameter being measurable by means of rotational viscometry at 110° C. and 30 s$^{-1}$ between two 20 mm plates.

The low molecular weight substance is preferably distributed finely in the polymer melt. For this purpose, it is possible to use known apparatus, for example stirrers which comprise a stirred tank with a propeller stirrer, disk stirrer, toothed disk stirrer, anchor stirrer, helical stirrer, blade stirrer, paddle stirrer, pitched-blade stirrer, cross-blade stirrer, spiral stirrer, MIG stirrer, INTERMIG stirrer, Ultra-Turrax stirrer, screw stirrer, belt stirrer, finger stirrer, basket stirrer, impeller stirrer, and also dispersers and homogenizers which can work, inter alia, with ultrasound. The apparatus may generally have at least one shaft on which in turn preferably 1 to 5 stirrer elements may be mounted.

This may give rise, for example, to a solution, a suspension or a dispersion, the particle size of the phase present in distributed form being preferably at most 5000 μm, more preferably at most 1000 μm, if the low molecular weight substance is present in particulate form.

The parameters necessary for this purpose depend on the apparatus detailed above. The stirrer speed may preferably be in the range from 10 to 25 000 revolutions per minute, more preferably in the range from 20 to 10 000 revolutions per minute.

The temperature at which the polymer melt is prepared may likewise be within a wide range, which depends upon factors including the solidification temperature of the hyperbranched polymer. The temperature is preferably in the range from −20° C. to 250° C., more preferably in the range from 0° C. to 200° C. In a particular aspect of the present invention, the temperature selected in the preparation of the polymer melt will be 10° C. to 200° C., more preferably in the range from 15° C. to 150° C., above the solidification temperature of the hyperbranched polymer. The pressure used in the preparation of the polymer melt is likewise uncritical, and depends in many cases on the type of low molecular weight substance and the solidification temperature of the hyperbranched polymer. For example, the pressure may be selected within the range from 0.1 mbar to 200 bar, preferably in the range from 10 mbar to 100 bar.

In a particular aspect of the present invention, preferably no solvent, especially no organic solvent, is added to the polymer melt, and particularly preferred polymer melts do not comprise any solvent. A solvent is understood here to mean a substance in which the hyperbranched polymer is soluble and which has to be removed during the preparation process, since this compound should not be present in the preparations. In this connection, it should be emphasized that many of the low molecular weight substances detailed above may have properties of a solvent. However, these substances are an intended constituent of the preparations, such that these compounds are not solvents in the context of the present invention. Accordingly, the use of solvents to perform the process is not necessary. On the other hand, some of the low molecular weight substances are supplied in dissolved form, in which case the solvents used for this purpose are generally uncritical for the use of the low molecular weight substance, such that they are, for example, not harmful to health if the low molecular weight substance is biologically active. Such auxiliaries need not necessarily be removed before the preparation of the polymer melt. Instead, these auxiliary substances may be incorporated into the polymer melt.

The polymer melt described above is, in accordance with the invention, converted to a second liquid phase in which the hyperbranched polymer is sparingly soluble and which has a solidification temperature below the solidification temperature of the hyperbranched polymer.

The term "sparingly soluble" means that the solubility of the hyperbranched polymer in the second liquid phase should be at a minimum. The solubility depends in many cases on the temperature. Accordingly, the dispersion conditions may in many cases be selected such that a minimum proportion of the hyperbranched polymer is dissolved in the second liquid phase. The hyperbranched polymer preferably has a solubility by the flask method at the dispersion temperature of at most 20 percent by mass, preferably at most 10 percent by mass, in the second liquid phase.

The second liquid phase has a solidification temperature below the solidification temperature of the hyperbranched polymer. In general, this temperature arises from the melting point or the glass transition temperature of the main constituent of the second liquid phase, and freezing point depressions as a result of auxiliaries or additives or as a result of the use of substance mixtures may occur. This parameter can be obtained from DSC measurements, the melting points or freezing points of the customary main constituents of the second liquid phase being listed in reference works.

The second liquid phase preferably comprises substances which are not harmful to health, and which more preferably have approval according to the Community Register of Feed Additives pursuant to Regulation (EC) No 1831/2003, Rev. 4 Status: Released 29 May 2006 (FDA).

When hydrophobic hyperbranched polymers are used, preferably at least one hydrophilic substance is used as the main constituent in the second liquid phase. The hydrophilic substances which may be present as the main constituent in the second liquid phase include especially water and alcohols having 1 to 7, preferably 1 to 4 carbon atoms, especially methanol, ethanol, propanol and/or butanol.

The second liquid phase may comprise, as well as the main constituent, additional auxiliaries, especially dispersants and stabilizers. These auxiliaries are known in the technical field, and dispersants counteract aggregation of the particles. These include especially emulsifiers, protective colloids and surfactants, each of which may be used according to the hyperbranched polymer used, low molecular weight substance and main constituent of the second liquid phase. The preferred surfactants include especially anionic surfactants such as lauryl ether sulfate, cationic surfactants and nonionic surfactants, for example polyvinyl alcohols and ethoxylated fatty alcohols. Stabilizers may be used for a multitude of uses, and these auxiliaries maintain or stabilize a desired unstable state. These include especially antisettling agents such as pectins and/or carrageenan.

The second liquid phase preferably comprises 60 to 100% by weight of main constituent, for example the hydrophilic substances detailed above, such as water or alcohols having up to 4 carbon atoms. In addition, the second liquid phase may contain 0 to 40% by weight of auxiliary substances, especially 0 to 20% by weight of emulsifiers and 0 to 20% by weight of stabilizers.

The polymer melt introduced into the second liquid phase is dispersed at a temperature which is greater than or equal to the solidification temperature of the hyperbranched polymer.

In the context of the present invention, the solidification temperature of the hyperbranched polymer refers to the temperature at which the hyperbranched polymer becomes solid, such that polymer particles at this temperature no longer agglomerate to larger aggregates without external actions. According to the structure and crystallization properties, the solidification temperature may result, for example, from the glass transition temperature or the melting point of the hyperbranched polymer, which can be determined, for example, by DSC processes (Differential Scanning calorimetry; Dynamic Difference calorimetry). In this context, it should be emphasized that partly crystalline polymers may exhibit both a glass transition temperature and a melting point, in which case the temperature at which the particles exhibit no agglomeration is crucial. If the surface is essentially crystalline, the melting point of these constituents is in many cases crucial.

In this connection, dispersion means that the polymer melt comprising at least one low molecular weight substance is distributed finely in the continuous second liquid phase. The dispersion can be performed here with known units and apparatus, for example stirrers which comprise a stirred tank with a propeller stirrer, disk stirrer, toothed disk stirrer, anchor stirrer, helical stirrer, blade stirrer, paddle stirrer, pitched-blade stirrer, cross-blade stirrer, spiral stirrer, MIG stirrer, INTERMIG stirrer, Ultra-Turrax stirrer, screw stirrer, belt stirrer, finger stirrer, basket stirrer, impeller stirrer, and also dispersers and homogenizers which can work, inter alia, with ultrasound. The apparatus may generally have at least one shaft on which in turn preferably 1 to 5 stirrer elements may be mounted.

The duration and the energy input of the dispersion are dependent here on the desired particle size and particle size distribution. Accordingly, the duration of the dispersion can be selected within a wide range. The dispersion is performed preferably for a duration in the range from 1 second to 5 hours, more preferably in the range from 10 seconds to 2 hours.

In a particular aspect, the polymer melt may comprise preferably 10 to 99.99% by weight, more preferably 50 to 99.00% by weight and most preferably to 90% by weight of hyperbranched polymer. In addition, the polymer melt may comprise preferably 0.01% by weight to 90% by weight, preferably 1% by weight to 50% by weight and most preferably 10% by weight to 30% by weight of low molecular weight substance.

In a particular aspect of the present invention, the Newton number in the course of dispersion may preferably be in the range from 0.1 to 1000, more preferably in the range from 0.4 to 800.

According to a particular embodiment of the process according to the invention, the Reynolds number in the course of dispersion may preferably be in the range from 1 to $10^7$, more preferably in the range from 10 to $10^6$.

The parameters needed for this purpose depend on the apparatus detailed above. The stirrer speed may preferably be in the range from 10 to 25 000 revolutions per minute, more preferably in the range from 20 to 10 000 revolutions per minute.

At the same time, the Newton number used and the stirrer speed depend on the desired particle size and particle size distribution. The more energy is supplied and the longer dispersion is effected, the smaller the particle sizes which can be achieved. A narrow particle size distribution can likewise be achieved by means of a high dispersion energy and a long dispersion time. On the other hand, long dispersion times and high dispersion energies are frequently associated with additional costs.

The temperature at which the polymer melt is dispersed in the second liquid phase may likewise be within a wide range, which depends upon factors including the solidification temperature of the hyperbranched polymer. The temperature is preferably in the range from −20° C. to 250° C., more preferably in the range from 0 to 200° C. The pressure used in the dispersion of the polymer melt is likewise uncritical, and in many cases depends on the type of low molecular weight substance and the solidification temperature of the hyperbranched polymer. For example, the pressure may be selected within the range from 10 mbar to 200 bar, preferably in the range from 100 mbar to 100 bar.

The temperature in the course of dispersion is greater than or equal to the solidification temperature of the hyperbranched polymer. The dispersion temperature is preferably 1° C. to 200° C., more preferably 5° C. to 150° C. and most preferably 10 to 50° C. above the solidification temperature of the hyperbranched polymer.

The weight ratio of polymer melt to the second liquid phase may be within a wide range. This ratio is preferably in the range from 1:1 to 1:1000, more preferably 1:1.5 to 1:500.

In the course of dispersion, the composition may comprise, for example, 50 to 99% by weight, preferably 70 to 98% by weight, of second liquid phase and 1 to 50% by weight, preferably 2 to 30% by weight, of polymer melt.

Once the polymer melt is present dispersed in the second liquid phase, the dispersed polymer melt is solidified. The solidification can be effected by known methods, for example by adding salts at a temperature slightly above the solidification temperature or by cooling. Preference is given to solidifying the polymer melt by cooling the second liquid phase to a temperature below the solidification temperature of the hyperbranched polymer.

The type of cooling depends on factors including the desired particle size and particle size distribution. Rapid cooling can lead, inter alia, to a particularly uniform particle size distribution and small particles, since aggregation can be prevented. At the same time, the formation of aggregates with a large cooling volume is lower.

In addition, the particle size distribution and the size of the particles can be influenced by means of auxiliaries, for example dispersants and emulsifiers. These additives may be added, for example, to the second phase, in which case additization of the surface of the particles formed can be achieved. This additization can also prevent aggregation of the microparticles during drying or in the course of storage.

According to the application, the composition thus obtained can be processed further directly without undertaking a purification, concentration or removal. In a particular embodiment, the present process may comprise the step of removing the microparticles formed in the second liquid phase. The removal can be effected by known processes, especially by filtration, centrifugation, sedimentation, magnet separation, flotation, screening or decanting, and the processes may be used individually or in combination. This can essentially completely remove the compounds of the second liquid phase, such that dried microparticles are obtained, or the particles can be concentrated, in which case even greater amounts of compounds of the second liquid phase are present in the end product. The end product may preferably have at least 80% by weight of microparticles, more preferably at least 95% by weight of microparticles.

The apparatus usable to remove or concentrate the microparticles, also referred to hereinafter as separators, are common knowledge. For instance, it is possible to use apparatus including centrifuges, decanters, centrifugal force separators, filters, for example gravity filters, suction filters (vacuum filters), pressure filters, suction/pressure filters, press filters, vacuum drum filters, belt filters, disk filters, planar filters, chamber filter presses, frame filter presses, candle filters, leaf filters, membrane filter plates and/or screening belt presses.

The temperature in the removal or concentration may likewise be within a wide range, and is dependent upon factors including the solidification temperature of the hyperbranched polymer. In order to prevent aggregation of the particles, the selected temperature should be below the solidification temperature of the hyperbranched polymer. The temperature is preferably in the range from −20° C. to 250° C., more preferably in the range from −10° C. to 100° C. The pressure used in the removal or concentration is likewise uncritical, and depends in many cases on the type of low molecular weight substance and the solidification temperature of the hyperbranched polymer. For example, the pressure may be selected within the range from 10 mbar to 200 bar, preferably in the range from 100 mbar to 100 bar.

After the removal, the resulting particles can be washed. To this end, the particles can be treated with a wash liquid in order to separate additive residues and/or low molecular weight substance which is present on the surface of the particles from the particles. Accordingly, the particles, especially the hyperbranched polymers, should not be soluble in the wash liquid. On the other hand, the substance to be removed, for example the low molecular weight substance, should have a maximum solubility. The preferred hydrophilic wash liquids include especially water and/or alcohols having 1 to 7, preferably 1 to 4 carbon atoms, especially methanol, ethanol, propanol and/or butanol. These liquids may be used individually or else as a mixture of two, three or more liquids.

The temperature in the course of washing may likewise be within a wide range, which depends upon factors including the solidification temperature of the hyperbranched polymer. In order to prevent aggregation of the particles, the selected temperature should be below the solidification temperature of the hyperbranched polymer. The temperature is preferably in the range from −20° C. to 250° C., more preferably in the range from −10° C. to 100° C. The pressure used in the washing is likewise uncritical, and depends in many cases on the type of low molecular weight substance and the solidification temperature of the hyperbranched polymer. For example, the pressure in the course of washing may be selected within the range from 10 mbar to 200 bar, preferably within the range from 100 mbar to 100 bar.

The apparatus usable to wash the particles are common knowledge. For example, it is possible for this purpose to use apparatus which comprise a mixing vessel and a separator. The mixing vessels preferably include the units and apparatus for dispersion detailed above. In addition, the mixing vessels may be equipped with temperature control. Accordingly, these mixing vessels may comprise heating elements or cooling elements.

In a further step, the resulting microparticles may be dried. The apparatus usable to dry the microparticles are common knowledge. For instance, it is possible to use apparatus including drum dryers, tumble dryers, pan dryers, screw dryers, paddle dryers, cylinder dryers, roll dryers, freeze dryers, fluidized bed dryers, spray dryers, flow dryers, grinding dryers, tray dryers, tunnel dryers, vacuum dryers and/or vacuum contact dryers.

The temperature in the course of drying may likewise be within a wide range, which depends upon factors including the solidification temperature of the hyperbranched polymer. In order to prevent aggregation of the particles, the selected temperature should be below the solidification temperature of the hyperbranched polymer. The temperature in the course of drying is preferably in the range from −20° C. to 150° C., more preferably in the range from −10° C. to 100° C. The pressure used in the course of drying is likewise uncritical, and depends in many cases on the type of low molecular weight substance and the solidification temperature of the hyperbranched polymer. For example, the pressure may be selected within the range from 0.1 mbar to 10 bar, preferably in the range from 0.2 mbar to 2 bar.

The process described above can be performed with simple systems which can be constructed from components known per se. Suitable systems preferably comprise at least two mixing vessels and a separator, in which case the mixing vessels are connected to one another via at least one feed line and the second mixing vessel is connected to the separator. The second phase removed in the separator can preferably be recycled into a mixing vessel via a recycle line.

In a preferred embodiment, a pump suitable for high-viscosity liquids may be provided in the line between the first mixing vessel in which the polymer melt is prepared and the second mixing vessel in which the polymer melt is dispersed in the second liquid phase. The preferred pumps include especially screw pumps, for example screw pumps with one, two or three screws, screw compressors, vane pumps, rotary piston pumps, rotary pumps, piston pumps and/or peristaltic pumps.

In a particular aspect of the present invention, the system preferably has at least three mixing vessels, in which case at least two mixing vessels are connected to at least one mixing vessel via feed lines. In this case, at least one mixing vessel serves to prepare the polymer melt, at least one mixing vessel to prepare the second liquid phase and at least one mixing vessel to disperse the polymer melt in the second liquid phase. The polymer melt and the second liquid phase may be prepared batchwise or continuously in further separate mixing vessels in order to ensure continuous production of microparticles.

The system may preferably have at least one dryer connected to the separator. In addition, the system may preferably comprise an apparatus for washing particles.

The solidification of the polymer melt in the dispersion can be achieved in the system by means of various measures. For example, it is possible to cool the mixing vessel in which the dispersion has been prepared. This can be done, for example, by external cooling or by supplying liquids which preferably have the same or a similar composition to the second liquid phase. For this purpose, it is preferably also possible to use a heat transferrer or heat exchanger, a mixing valve or an additional mixing vessel.

The system may comprise pumps which may serve, for example, for the transport of liquids or for the generation of elevated or reduced pressure. Suitable pumps depend on the particular purpose. The preferred pumps include, for example, displacer pumps, for example drawing machines, conveying screws, bellows pumps, piston pumps, rotary piston pumps, externally/internally toothed gear pumps, membrane pumps, rotary vane pumps, centrifugal pumps, peristaltic pumps, toothed belt pumps, eccentric spiral pumps, screw pumps and screw compressors and/or hydraulic rams;
flow pumps, for example centrifugal pumps, axial pumps, diagonal pumps, and/or radial pumps;
bubble pumps, water-jet pumps, vapor jet pumps, hydraulic rams, horsehead pumps (depth pumps);
vacuum pumps, for example displacer pumps, propellant pumps, molecular pumps, turbomolecular pumps, cryopumps, sorption pumps, oil diffusion pumps.

Figure 1:
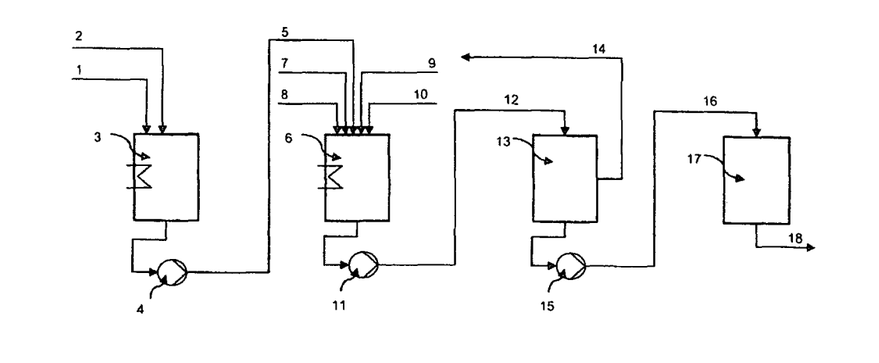
FIG. 1 shows an apparatus for performing the process of the present invention.

FIG. 1 shows a first embodiment of a system for performing the process of the present invention. This system may have, for example, one, two or more feeds 1 or 2, for example lines or feed screws, through which one or more hyperbranched polymers and/or one or more low molecular weight substances are supplied to a first mixing vessel 3. In the mixing vessel 3, the substances supplied can be converted to a polymer melt which comprises at least one hyperbranched polymer and at least one low molecular weight substance. In mixing vessel 3, the components can be finely distributed within one another. For example, a solution, a dispersion or suspension can be prepared. In many cases, the hyperbranched polymer forms the matrix phase in which the low molecular weight substance is distributed. For this purpose, it is possible to use the apparatus described above.

The polymer melt obtained in mixing vessel 3 can, for example, be transferred to the mixing vessel 6 with a pump 4 via the feed 5, for example a line.

The mixing vessel 6 may have one, two, three, four or more further feeds 7, 8, 9, 10, for example lines or feed units, such as screws or pumps, through which, for example, stabilizers, emulsifiers, warm water and/or cold water can be supplied. In the present description of the figures, water is used by way of example as a second liquid phase. However, it is obvious to those skilled in the art that any other compound described above as a main constituent of the second liquid phase may likewise be used instead of or together with water. The water thus serves merely as an example of the compounds detailed above, which can correspondingly be replaced by the other substances.

The feeds 7, 8, 9, 10 can all open in the mixing vessel 6. In addition, these feeds may also be combined upstream of entry into the mixing vessel 6.

Before the polymer melt is fed into the mixing vessel 6, it is possible, for example, through feeds 7, 8 and 9, to prepare a solution which comprises, as a main constituent, for example, water or ethanol, and auxiliaries, for example stabilizers and emulsifiers. This solution can be heated to a temperature above the solidification temperature of the hyperbranched polymer. In addition, the components supplied may already have an appropriate temperature.

After an appropriate solution has been prepared in mixing vessel 6, the polymer melt prepared in mixing vessel 3 can be supplied to the mixing vessel 6. In mixing vessel 6, the polymer melt is dispersed in the solution described above. For this purpose, the mixing vessel 6 has known apparatus for dispersion. For this purpose, the apparatus described above may be used.

Once the desired droplet size and droplet size distribution has been obtained through the dispersion, the polymer melt present dispersed in the second liquid phase, for example water, can be solidified. To this end, for example, cold water can be introduced into the mixing vessel 6 via a feed 10. In addition, the mixing vessel 6 may be cooled by means of a cooling medium which is passed through a heat exchanger or a jacket.

The particles thus obtained can be removed from the second liquid phase. To this end, the composition which has been obtained in mixing vessel 6 and comprises solidified microparticles can, for example, be transferred into the separator 13 via the line 12 with a pump 11. The separator 13 serves to remove or concentrate the microparticles present in the second liquid phase, for which any of the apparatuses detailed above can be used. In the present case, in the separator, the microparticles are separated from the second liquid phase, for which a concentration may be sufficient in many cases. The removed second liquid phase, which may comprise, for example, water, emulsifiers and stabilizers, can be introduced into the mixing vessel 6 via a recycle line 14.

The removed microparticles may, for example, be transferred into the dryer 17 with a pump 15 via the feed 16, for example a line. In the dryer 17, residues of the second liquid phase, for example water, can be removed. The dried microparticles can be removed from the dryer via the line 18.

The temperatures in the course of loading may be within a wide range. Preference is given to performing the loading at a temperature in the range from −10° to 150° C., more preferably from 0° C. to 80° C.

The inventive preparations may have a surprisingly high proportion of low molecular weight substance. In a particular aspect of the present invention, the weight ratio of hyperbranched polymer to the low molecular weight substance may preferably be in the range from 40:1 to 0.5:1, more preferably in the range from 20:1 to 2:1. The degree of loading may preferably be within a range of from 1% to 99%, more preferably from 5% to 90% and very particularly from 10 to 30%, the degree of loading being given by the proportion by weight of the low molecular weight substance in the total weight of the preparation.

The low molecular weight substances can be released from the inventive combination or the inventive preparation in a desired manner. For example, an enzymatic degradation can be used in order to release the low molecular weight substance. In this case, the release period can be controlled by the degradation rate.

Furthermore, the release can be controlled precisely via a change in the pH, temperature, pH, radiation frequency and type of the medium.

The type of medium can be altered, for example, via the addition of solvents.

The solvents used to vary the medium may include water, alcohols such as ethanol or isopropanol, compressed $CO_2$, compressed propane, tetrahydrofuran, toluene, acetone, benzoyl peroxide, aqueous HCl solutions, hexane, acetic acid, ethanediol, dichloromethane, dichloroethane or ionic liquids.

According to the degree of functionalization of the hyperbranched polymer and the medium into which the low molecular weight substance is to be released, it is thus possible to add a wide variety of different solvents in order to achieve a very retarded or very rapid release. If the encapsulated low molecular weight substances are to be released into polar media, the more OH groups of the hyperbranched core polyester have been esterified/functionalized with fatty acids, the slower the release. This effect can be promoted by addition of appropriate solvents.

Moreover, the active ingredient release can be controlled especially through the thickness of the carrier polymer shell which surrounds the low molecular weight substance or the active ingredient and/or the degree of functionalization/degree of hydrophobization or the hydroxyl number of the hyperbranched polymer.

The thicker the carrier polymer shell is, the greater the release period. The thickness of the carrier polymer shell can be increased especially by increasing the polymer concentration in the starting mixture (consisting of at least one hyperbranched polymer and a low molecular weight substance). In this case, the type of encapsulation process can have an influence on this parameter, and the person skilled in the art can select the most viable process from those specified above for the given purpose by simple routine tests.

It has been found that, surprisingly, in the case of hyperbranched carrier polymers, the concentration in the starting mixture (consisting of solvent+carrier polymer+low molecular weight substance) can also be increased above the polymer concentrations customary in the prior art of 10% by mass up to a polymer concentration of 70% by mass. The ultimately selected polymer concentration, together with the temperature control and alteration of pH or dissolution power of the solvent, decides the thickness of the polymer shell and hence the release period.

In addition to the thickness of the carrier polymer shell, the degree of functionalization or the hydroxyl number decides the release period. If the encapsulated low molecular weight substances are to be released in polar media, the more OH groups of the hyperbranched core polyester have been esterified/functionalized with fatty acids, the slower the release.

The preparations of the present invention may have various uses. For example, the preparations may be used as a hardener, as a crosslinker, as a catalyst, as a defoamer, as a dispersant, as an additive with antimicrobial or antifungicidal action, as an additive for increasing the scratch resistance of surfaces, as an additive in coatings or adhesives, as a flow improver and/or as a concrete additive. In addition, the preparations may be used in cosmetics, in medicaments, in deodorants, in foods, in animal feeds, in drinks, in wall or floor coverings, in joint materials, in packaging and/or in paint systems.

In a particular aspect of the present invention, the preparation comprises preferably only small amounts of creatine, folic acid or tocopherol, if these substances are used alone as the low molecular weight substance. More preferably, the amount of keratin, folic acid or tocopherol is restricted to 10% by weight, more preferably 5% by weight, based on the weight of the preparation, if the preparation does not comprise any further low molecular weight substances. Preparations which comprise combinations of creatine, folic acid and/or tocopherol with one another or with further low molecular weight substances are, however, preferred, in which case these preparations may also comprise more than 10% by weight of keratin, folic acid or tocopherol.

The present invention will be illustrated in detail hereinafter by examples, without any intention that this should impose a restriction.

EXAMPLES

Example 1

Using the system shown in FIG. 1, an inventive preparation which comprised DL-methionine and a hyperbranched polyester was prepared.

The hyperbranched polyester used was obtained (commercially from Perstorp® under the name Boltorn H30®) by hydrophobizing a hydrophilic hyperbranched polyester which had a weight-average molecular weight $M_w$ of 3500 g/mol, a glass transition temperature of about 35° C. and a hydroxyl number of about 490 mg KOH/g. The hydrophobization was effected by esterifying the hydrophilic polymer with a mixture of eicosanoic acid and behenic acid (mass-based ratio of eicosanoic acid to behenic acid=2 to 3), and 90% of the hydroxyl groups of the hydrophilic polymer were converted. The molecular weight $M_w$ was 10 500 g/mol. Further details of the preparation of the hydrophilic polymer and of the esterification can be taken from the documents EP-B1-0630389 or WO 93/01760.

To produce the preparation, 20% by weight of the amino acid DL-methionine (CAS: 59-51-8; commercially available from Degussa® AG; ground, particle size d90 in the range from 1 μm to 100 μm) was dispersed in the molten polymer at a temperature of about 95° C. with a spiral stirrer at 200 revolutions per minute in a first mixing vessel for 5 minutes.

A further mixing vessel was initially charged with a mixture of surfactants consisting of 1% by weight of polyvinyl alcohol (M=6000 g/mol, Polisciences®, Warrington, USA) and 0.1% by weight of an ethoxylated fatty alcohol (Tego® Alkanol L4 from Degussa® AG) in water at 70° C. with stirring.

Subsequently, the polymer melt which had been prepared in the first mixing vessel and comprised, as well as the polymer, also the low molecular weight substance was transferred from the first mixing vessel to the second mixing vessel at 70° C. with continuing stirring with an Ultra-Turrax stirrer at 2000 revolutions per minute.

After a residence time of 0.5 to 10 minutes and cooling of the composition present in the second mixing vessel to a temperature which was 15° C. below the melting point of the polymer, particles formed. A peristaltic pump was used to feed the suspension to a centrifuge in which the active ingredient particles were removed at 25° C. from the continuous phase. Subsequently, the active ingredient particles were dried in a vacuum dryer at 25° C. and 10 mbar for 100 h.

These particles exhibited a particle size distribution of 200 μm<$d_{90,particles}$<300 μm. The particles were free of undesired solvents and consisted of the hyperbranched fatty acid-modified polyester and approx. 12% by weight of DL-methionine based on the particle mass.

Example 2

Example 1 was essentially repeated, except that a hyperbranched polyester was used which had been obtained by hydrophobizing Boltorn H30® with a mixture of stearic acid and palmitic acid (mass-based ratio of stearic acid to palmitic acid=2:1), and 50% of the hydroxyl groups of the hydrophilic polymer were converted. The molecular weight $M_w$ was 7500 g/mol.

The resulting particles exhibited a particle size distribution of 150 µm<$d_{90,particles}$<300 µm. The particles were free of undesired solvents and consisted of the hyperbranched fatty acid-modified polyester and approx. 16% by weight of DL-methionine based on the particle mass.

The storage stability, the shear stability and the enzymatic degradability of the resulting microparticles were investigated.

The storage stability was determined by storing the dry microparticles in a glass vessel, and the storage was effected at room temperature in an oxygenous atmosphere (air). After a storage time of 6 months, the methionine content determined chromatographically by means of HPLC was at least 98% of the original value.

To investigate the shear stability, a dispersion of the resulting microparticles in a pharmaceutical oil (Paraffin Oil WINOG 100 Pharma from Univar® GmbH) was prepared. To this end, the particles were incorporated into a standard pharmaceutical oil (Paraffin Oil WINOG 100 Pharma from Univar® GmbH) with an Ultra-Turrax stirrer which stirred at 20 000 revolutions per minute for one minute. A comparison of the microscope images of the active ingredient particles before and after the incorporation into the standard pharmaceutical oil showed that no change in the particle integrity can be seen and the protective action for the biologically active ingredient DL-methionine was thus maintained.

The enzymatic release of the active ingredient present in the microparticles was effected with a lipase. To this end, 0.22 g of microparticles was suspended in 15 ml of solution of the enzyme Lipomod 34P (Biocatalyst Lmt., UK) in phosphate buffer (pH 5.01) (the concentration of the Lipomod 34P was 0.5 mg/ml). The sample was stored in a water bath at 37° C. without mixing. At regular time intervals, a sample of ml was taken. The concentration of the active ingredient was analyzed chromatographically by means of HPLC. After 24 hours, approx. 70% of the encapsulated methionine had been released. In contrast, less than 20% of the encapsulated methionine had been released into the enzyme-free buffer solution after 24 hours.

Example 3

Example 2 was essentially repeated, except that L-leucine (CAS: 61-90-5; commercially available from Degussa® AG; particle size d90 in the range from 1 µm to 10 µm) was used instead of DL-methionine. In this case, the polymer melt was prepared at a temperature of about 85° C. In addition, the Ultra-Turrax stirrer, in the transfer of the polymer melt into the second liquid phase, was operated at 3000 revolutions per minute.

The resulting particles exhibited a particle size distribution of 10 µm<$d_{90,particles}$<50 µm. The particles were free of undesired solvents and consisted of the hyperbranched fatty acid-modified polyester and approx. 16% by weight of L-leucine based on the particle mass.

In the shear stability study, these microparticles likewise exhibited a high stability. A comparison of the microscope images of the active ingredient particles before and after the incorporation into the standard pharmaceutical oil showed that no change in the particle integrity can be seen and the protective action for the biologically active ingredient L-leucine was thus maintained.

Example 4

Example 2 was essentially repeated, except that L-lysine (CAS: 56-87-1; ground; 50% by weight; obtainable commercially from Degussa® AG; particle size d90 in the range from 1 µm to 10 µm) was used instead of DL-methionine. In this case, the polymer melt was prepared at a temperature of about 85° C.

The resulting particles exhibited a particle size distribution of 150 µm<$d_{90,particles}$<300 µm. The particles were free of undesired solvents and consisted of the hyperbranched fatty acid-modified polyester and approx. 8% by weight of L-lysine based on the particle mass.

In the shear stability study, these microparticles likewise exhibited a high stability. A comparison of the microscope images of the active ingredient particles before and after the incorporation into the standard pharmaceutical oil showed that no change in the particle integrity can be seen and the protective action for the biologically active ingredient L-lysine was thus maintained.

Example 5

Example 1 was essentially repeated, except that a hyperbranched polyester which had been obtained by hydrophobizing Boltorn H30® with a mixture of stearic acid and palmitic acid (mass-based ratio of stearic acid to palmitic acid=2 to 1) was used, and 95% of the hydroxyl groups of the hydrophilic polymer had been converted. The molecular weight $M_w$ was 10 000 g/mol. In addition, L-tryptophan (CAS: 73-22-3; obtainable commercially from Degussa® AG; particle size d90 in the range from 1 µm to 10 µm) was used instead of DL-methionine as the low molecular weight substance. In this case, the polymer melt was prepared at a temperature of about 85° C. In addition, the Ultra-Turrax stirrer, in the transfer of the polymer melt into the second liquid phase, was operated at 3000 revolutions per minute.

The resulting particles exhibited a particle size distribution of 10 µm<$d_{90,particles}$<60 µm. The particles were free of undesired solvents and consisted of the hyperbranched fatty acid-modified polyester and approx. 16% by weight of L-tryptophan based on the particle mass.

In the shear stability study, these microparticles likewise exhibited a high stability. A comparison of the microscope images of the active ingredient particles before and after the incorporation into the standard pharmaceutical oil showed that no change in the particle integrity can be seen and the protective action for the biologically active ingredient L-tryptophan was thus maintained.

Example 6

Example 5 was essentially repeated, except that a banana extract solution (20% by weight of banana extract in ethanol) was used instead of L-tryptophan. In this case, 20% by volume of banana extract solution was dissolved in the molten polymer.

The resulting particles exhibited a particle size distribution of 10 µm<$d_{90,particles}$<60 µm. The particles were free of undesired solvents and consisted of the hyperbranched fatty acid-modified polyester and approx. 3% by weight of banana extract based on the particle mass.

Example 7

Example 5 was essentially repeated, except that a combination of strawberry extract solution (20% by weight of strawberry extract in ethanol) and creatine (Creapure, CAS: 50-00-1, ground, obtainable commercially from Degussa® AG; particle size d90 in the range from 0 µm to 10 µm) was used instead of L-tryptophan. In this case, 5% by volume of strawberry extract solution and 20% by weight of creatine were dissolved in the molten polymer.

The resulting particles exhibited a particle size distribution of 10 μm<$d_{90,particles}$<60 μm. The particles were free of undesired solvents and consisted of the hyperbranched fatty acid-modified polyester and approx. 0.8% by weight of strawberry extract and 16% by weight of creatine based on the particle mass.

Example 8

Example 5 was essentially repeated, except that a combination of L(+)-ascorbic acid (vitamin C, CAS: 50-81-7, ground, commercially available from AcrosOrganics®, particle size d90 in the range from 0 μm to 10 μm) and creatine (Creapure, CAS: 50-00-1, ground, obtainable commercially from Degussa® AG; particle size d90 in the range from 0 μm to 10 μm) was used instead of L-tryptophan. In this case, 10% by weight of L(+)-ascorbic acid and 10% by weight of creatine were dispersed in the molten polymer.

The resulting particles exhibited a particle size distribution of 10 μm<$d_{90,particles}$<50 μm. The particles were free of undesired solvents and consisted of the hyperbranched fatty acid-modified polyester and approx. 8% by weight of L(+)-ascorbic acid and 8% by weight of creatine based on the particle mass.

Example 9

Example 5 was essentially repeated, except that a combination of lemon aroma solution (20% by weight of lemon aroma in ethanol) and percarbonate (sodium percarbonate for laundry detergents, obtainable commercially from AcrosOrganics®; particle size d90 in the range from 1 μm to 10 μm) was used instead of L-tryptophan. In this case, 5% by volume of lemon aroma solution and 20% by weight of sodium percarbonate were dissolved in the molten polymer. In addition, the ULTRA-TURRAX stirrer, in the transfer of the polymer melt into the second liquid phase, was operated at 2000 revolutions per minute.

The resulting particles exhibited a particle size distribution of 10 μm<$d_{90,particles}$<60 μm. The particles were free of undesired solvents and consisted of the hyperbranched fatty acid-modified polyester and approx. 0.8% by weight of lemon aroma and 16% by weight of sodium percarbonate based on the particle mass.

Example 10

Example 2 was essentially repeated, except that ammonium persulfate (CAS: 7727-54-0; obtainable commercially from Degussa® AG; particle size d90 in the range from 1 μm to 200 μm) was used instead of DL-methionine. In this case, the polymer melt was prepared at a temperature of about 70° C.

The resulting particles exhibited a particle size distribution of 250 μm<$d_{90,particles}$<400 μm. The particles were free of undesired solvents and consisted of the hyperbranched fatty acid-modified polyester and approx. 16% by weight of ammonium persulfate, based on the particle mass.

Example 11

Example 2 was essentially repeated, except that L-tryptophan (CAS: 73-22-3; obtainable commercially from Degussa® AG; particle size d90 in the range from 1 μm to 10 μm) was used instead of DL-methionine. In this case, the polymer melt was prepared at a temperature of about 85° C. In addition, the Ultra-Turrax stirrer, in the transfer of the polymer melt into the second liquid phase, was operated at 1000 revolutions per minute.

The resulting particles exhibited a particle size distribution of 300 μm<$d_{90,particles}$<500 μm. The particles were free of undesired solvents and consisted of the hyperbranched fatty acid-modified polyester and approx. 16% by weight of L-tryptophan based on the particle mass. This example shows that the particle size can be adjusted readily to a desired value by the process according to the invention, and large particles, for example, do not exhibit any dust formation.

The invention claimed is:

1. A preparation comprising at least one low molecular weight substance having a molar mass of from 15 g/mol to 1000 g/mol and at least one hyperbranched polymer, wherein said hyperbranched polymer comprises:
    a) a hydrophilic core having polyester units and hydrophobic end groups;
    b) a molecular weight greater than or equal to 6000 g/mol and a hydroxyl number in the range of from 0 to 200 mg KOH/g;
    c) a degree of branching in the range of from 20 to 70%; and
    d) a melting point of at least 30° C.;
and wherein said preparation is in the form of particles having a size in the range of from 1 to 1000 μm and in which said low molecular substance is embedded in a shell which comprises said hyperbranched polymer, said preparation being made by a process comprising:
    (i) preparing a polymer melt comprising at least one hyperbranched polymer and at least one low molecular weight substance;
    (ii) introducing said polymer melt into a second liquid phase in which said hyperbranched polymer is sparingly soluble and which has a solidification temperature below the solidification temperature of said hyperbranched polymer, said second liquid phase comprising 60 to 100% by weight of water, alcohols having up to 4 carbon atoms or combinations thereof;
    (iii) dispersing said polymer melt in said second liquid phase at a temperature which is greater than or equal to the solidification temperature of said hyperbranched polymer; and
    (iv) solidifying said polymer melt dispersed in said second liquid phase.

2. The preparation of claim 1, wherein said hyperbranched polymer has a degree of functionalization of at least 30% and a water solubility by the flask method at 40° C. of at most 10% by mass.

3. The preparation of claim 1, wherein said hydrophilic core has at least 90% by weight of repeat units derived from polyester-forming monomers.

4. The preparation of claim 1, wherein said hydrophilic core comprises a central unit derived from an initiator molecule having at least two hydroxyl groups, and repeat units derived from monomers having at least one carboxyl group and at least two hydroxyl groups.

5. The preparation of claim 4, wherein said initiator molecule is selected from the group consisting of: an aliphatic polyol; ditrimethylolpropane;
    ditrimethylolethane; dipentaerythritol; pentaerythritol; alkoxylated pentaerythritol;
    trimethylolethane; trimethylolpropane; alkoxylated trimethylolpropane; glycerol;
    neopentyl alcohol; dimethylolpropane; and 1,3-dioxane-5, 5-dimethanol.

6. The preparation of claim 4, wherein said monomers are selected from the group consisting of: dimethylpropionic acid; α,α-bis(hydroxymethyl)-butyric acid; α,α,α-tris-(hydroxymethyl)acetic acid; α,α-bis(hydroxymethyl)valeric acid; α,α-bis(hydroxy)-propionic acid; and 3,5-dihydroxybenzoic acid.

7. The preparation of claim 1, wherein said hydrophobic end groups are formed by groups derived from carboxylic acids selected from the group consisting of: decanoic acid; dodecanoic acid; tetradecanoic acid; hexadecanoic acid; heptadecanoic acid; octadecanoic acid; eicosanoic acid; docosanoic acid and tetracosanoic acid.

8. The preparation of claim 1, wherein said hyperbranched polymer has an acid number in the range of from 0 to 20 mg KOH/g or a melting point of at most 57° C.

9. The preparation of claim 1, wherein said hydrophilic core has a hydroxyl number, measured before the hydrophobization, in the range from 400 to 600 mg KOH/g.

10. The preparation of claim 1, wherein said low molecular weight substance is selected from the group consisting of: a compound having a peroxide group;
an amino acid; a catalyst; a dye or pigment; a vitamin; a monomer; flavoring or aroma enhancing agent; a medicament; an enzyme; a coenzyme; a plant extract; an initiator; a silicone; a surfactant; a silica; a silane; a solvent; a filler; a reactive crosslinker; a detergent; a hair dye; and a concrete additive.

11. The preparation of claim 1, wherein said hyperbranched polymer is enzymatically degradable.

12. The preparation of claim 1, wherein said preparation is in the form of particles with a size in the range of from 1 μm to 1000 μm and at least 80% by weight of said particles are within a size range of from 1 μm to 100 μm.

13. The preparation of claim 1, wherein said hyperbranched polymer, at 48° C. in a 50% by weight/50% by weight mixture with water, has only liquid-liquid equilibria, but no solid-liquid equilibria, solid-liquid-liquid equilibria.

14. The preparation of claim 1, wherein said preparation is part of a product selected from the group consisting of: a hardener; a crosslinker; a catalyst; a defoamer; a dispersant; an additive with antimicrobial or antifungicidal action; an additive for increasing the scratch resistance of surfaces; an additive in coatings or adhesives; a flow improver; a concrete additive; a cosmetic; a medicament; a deodorant; a food; an animal feed; a beverage; a wall or floor covering; a joint material; and a packaging or in paint system.

15. A process for producing a preparation comprising a low molecular weight substance embedded in a shell comprising a hyperbranched polymer, said process comprising the steps of:
(a) preparing a polymer melt comprising at least one hyperbranched polymer and a low molecular weight substance having a molar mass of from 15 g/mol to 1000 g/mol wherein said hyperbranched polymer comprises;
i) a hydrophilic core having polyester units and hydrophobic end groups;
ii) a molecular weight greater than or equal to 6000 g/mol and a hydroxyl number in the range of from 0 to 200 mg KOH/g;
iii) a degree of branching in the range of from 20 to 70%; and
iv) a melting point of at least 30° C.;
(b) introducing said polymer melt into a second liquid phase in which said hyperbranched polymer is sparingly soluble and which has a solidification temperature below the solidification temperature of said hyperbranched polymer, said second liquid phase comprising 60 to 100% by weight of water, alcohols having up to 4 carbon atoms or combinations thereof;
(c) dispersing said polymer melt in said second liquid phase at a temperature which is greater than or equal to the solidification temperature of said hyperbranched polymer; and
(d) solidifying said polymer melt dispersed in said second liquid phase.

16. The process of claim 15, wherein said hydrophilic core has at least 90% by weight of repeat units derived from polyester-forming monomers.

17. The process of claim 15, wherein said hyperbranched polymer has a degree of functionalization of at least 30% and a water solubility by the flask method at 40° C. of at most 10% by mass.

18. The process of claim 15, wherein said hydrophobic end groups are formed by groups derived from carboxylic acids selected from the group consisting of: decanoic acid; dodecanoic acid; tetradecanoic acid; hexadecanoic acid; heptadecanoic acid; octadecanoic acid; eicosanoic acid; docosanoic acid and tetracosanoic acid.

19. The process of claim 15, wherein said low molecular weight substance is selected from the group consisting of: a compound having a peroxide group;
an amino acid; a catalyst; a dye or pigment; a vitamin; a monomer; flavoring or aroma enhancing agent; a medicament; an enzyme; a coenzyme; a plant extract; an initiator; a silicone; a surfactant; a silica; a silane; a solvent; a filler; a reactive crosslinker; a detergent; a hair dye; and a concrete additive.

20. The preparation of claim 15, wherein said preparation is in the form of particles with a size in the range of from 1 μm to 1000 μm and at least 80% by weight of said particles are within a size range of from 1 μm to 100 μm.

* * * * *